US011690642B2

(12) United States Patent
Black et al.

(10) Patent No.: US 11,690,642 B2
(45) Date of Patent: Jul. 4, 2023

(54) ULTRASONIC SURGICAL INSTRUMENT WITH A MULTI-PLANAR ARTICULATING SHAFT ASSEMBLY

(71) Applicant: Cilag GmbH International, Zug (CH)

(72) Inventors: Brian D. Black, Loveland, OH (US); Morgan R. Hunter, Cincinnati, OH (US); Thomas B. Remm, Milford, OH (US)

(73) Assignee: Cilag GmbH International, Zug (CH)

( * ) Notice: Subject to any disclaimer, the term of this patent is extended or adjusted under 35 U.S.C. 154(b) by 638 days.

(21) Appl. No.: 16/556,661

(22) Filed: Aug. 30, 2019

(65) Prior Publication Data

US 2021/0059709 A1 Mar. 4, 2021

(51) Int. Cl.
*A61B 17/32* (2006.01)
*A61B 18/14* (2006.01)
(Continued)

(52) U.S. Cl.
CPC .. *A61B 17/320092* (2013.01); *A61B 18/1445* (2013.01); *A61B 2017/00477* (2013.01); (Continued)

(58) Field of Classification Search
CPC ........ A61B 17/320092; A61B 18/1445; A61B 2017/00477; A61B 2017/320069; A61B 2017/320071; A61B 2017/320074; A61B 2017/320089; A61B 2017/320093; A61B 2017/320094; A61B 2017/320095; A61B 2018/00589; A61B 34/70; A61B 2017/00314; A61B 2017/00318; A61B 2017/22018; A61B 2017/2908

See application file for complete search history.

(56) References Cited

U.S. PATENT DOCUMENTS

| 5,322,055 A | 6/1994 | Davison et al. |
| 5,873,873 A | 2/1999 | Smith et al. |

(Continued)

OTHER PUBLICATIONS

U.S. Appl. No. 16/556,625, entitled "Ultrasonic Surgical Instrument with Axisymmetric Clamping," filed Aug. 30, 2019.

(Continued)

*Primary Examiner* — Ashley L Fishback
(74) *Attorney, Agent, or Firm* — Frost Brown Todd LLP

(57) ABSTRACT

An ultrasonic surgical instrument and method of deflecting an end effector include an acoustic waveguide with a proximal waveguide body portion defining a longitudinal axis, a distal waveguide body portion having an ultrasonic blade distally projecting therefrom, and an articulation body portion extending between the proximal and distal waveguide body portions. The articulation body portion of the acoustic waveguide is configured to flex a first direction to thereby deflect the ultrasonic blade relative to the longitudinal axis and through a first plane. In addition, the articulation body portion of the acoustic waveguide is further configured to flex a second direction to thereby deflect the ultrasonic blade relative to the longitudinal axis and through a second plane. The second direction is different than the first direction such that the second plane is different than the first plane for multiplanar deflection of the ultrasonic blade relative to the longitudinal axis.

19 Claims, 22 Drawing Sheets

(51) Int. Cl.
    *A61B 17/00*         (2006.01)
    *A61B 18/00*         (2006.01)

(52) U.S. Cl.
    CPC ............ *A61B 2017/320069* (2017.08); *A61B 2017/320071* (2017.08); *A61B 2017/320074* (2017.08); *A61B 2017/320089* (2017.08); *A61B 2017/320093* (2017.08); *A61B 2017/320094* (2017.08); *A61B 2017/320095* (2017.08); *A61B 2018/00589* (2013.01)

(56) References Cited

U.S. PATENT DOCUMENTS

| | | |
|---|---|---|
| 5,980,510 A | 11/1999 | Tsonton et al. |
| 6,063,098 A * | 5/2000 | Houser .................... B06B 3/00 606/169 |
| 6,325,811 B1 | 12/2001 | Messerly |
| 6,500,176 B1 | 12/2002 | Truckai et al. |
| 6,773,444 B2 | 8/2004 | Messerly |
| 6,783,524 B2 | 8/2004 | Anderson et al. |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 8,461,744 B2 | 6/2013 | Wiener et al. |
| 8,479,969 B2 | 7/2013 | Shelton, IV |
| 8,573,461 B2 | 11/2013 | Shelton, IV et al. |
| 8,573,465 B2 | 11/2013 | Shelton, IV |
| 8,591,536 B2 | 11/2013 | Robertson |
| 8,602,288 B2 | 12/2013 | Shelton, IV et al. |
| 8,616,431 B2 | 12/2013 | Timm et al. |
| 8,623,027 B2 | 1/2014 | Price et al. |
| 8,663,220 B2 | 3/2014 | Wiener et al. |
| 8,783,541 B2 | 7/2014 | Shelton, IV et al. |
| 8,800,838 B2 | 8/2014 | Shelton, IV |
| 8,820,605 B2 | 9/2014 | Shelton, IV |
| 8,844,789 B2 | 9/2014 | Shelton, IV et al. |
| 8,911,460 B2 | 12/2014 | Neurohr et al. |
| 9,023,071 B2 | 5/2015 | Miller et al. |
| 9,095,367 B2 | 8/2015 | Olson et al. |
| 9,301,759 B2 | 4/2016 | Spivey et al. |
| 9,381,058 B2 | 7/2016 | Houser et al. |
| 9,393,037 B2 | 7/2016 | Olson et al. |
| 9,402,682 B2 | 8/2016 | Worrell et al. |
| 9,949,785 B2 | 4/2018 | Price et al. |
| 10,034,683 B2 | 7/2018 | Monroe et al. |
| 10,172,636 B2 | 1/2019 | Stulen et al. |
| 10,226,274 B2 | 3/2019 | Worrell et al. |
| 10,342,567 B2 | 7/2019 | Hibner et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2011/0087212 A1 | 4/2011 | Aldridge et al. |
| 2012/0116265 A1 | 5/2012 | Houser et al. |
| 2014/0005681 A1 * | 1/2014 | Gee .................... A61F 9/00745 606/130 |
| 2014/0005702 A1 * | 1/2014 | Timm .................... A61B 17/29 606/169 |
| 2015/0320438 A1 | 11/2015 | Weisenburgh, II et al. |
| 2016/0302818 A1 | 10/2016 | Weisenburgh, II et al. |
| 2016/0302819 A1 | 10/2016 | Stulen et al. |
| 2017/0105757 A1 * | 4/2017 | Weir .................... A61B 34/30 |
| 2017/0281217 A1 | 10/2017 | Hibner |
| 2017/0281218 A1 | 10/2017 | Timm |
| 2017/0281219 A1 | 10/2017 | Hibner et al. |
| 2017/0281220 A1 | 10/2017 | Hibner et al. |
| 2017/0281221 A1 | 10/2017 | Boudreaux |
| 2019/0059931 A1 | 2/2019 | Shelton, IV et al. |

OTHER PUBLICATIONS

U.S. Appl. No. 16/556,635, entitled "Ultrasonic Blade and Clamp Arm Alignment Features," filed Aug. 30, 2019.
U.S. Appl. No. 16/556,667, entitled "Ultrasonic Transducer Alignment of an Articulating Ultrasonic Surgical Instrument," filed Aug. 30, 2019.
U.S. Appl. No. 16/556,727, entitled "Rotatable Linear Actuation Mechanism," filed Aug. 30, 2019.
U.S. Appl. No. 61/410,603, entitled "Energy-Based Surgical Instruments," filed Nov. 5, 2010.
European Search Report and Written Opinion dated Jan. 18, 2023 for Application No. EP 22202107.3, 10 pgs.
International Search Report and Written Opinion dated Dec. 14, 2020 for Application No. PCT/IB2020/057737, 16 pgs.

* cited by examiner

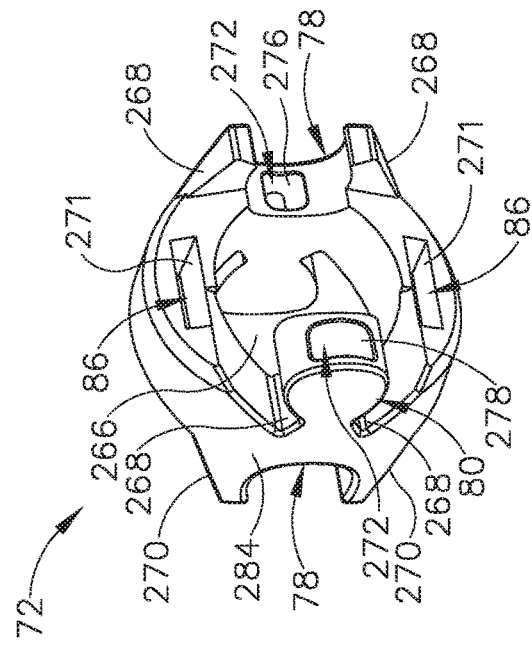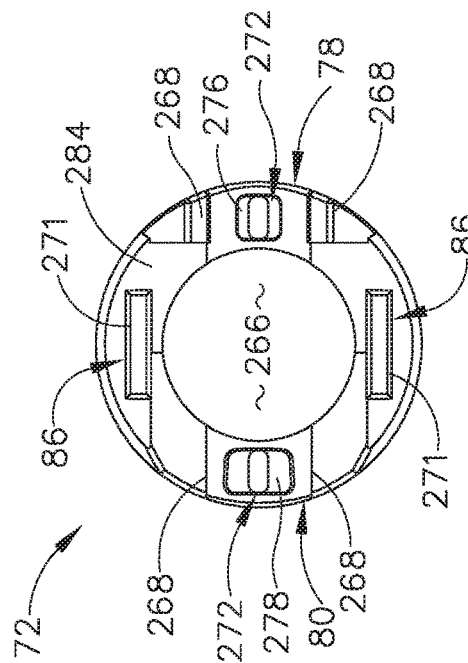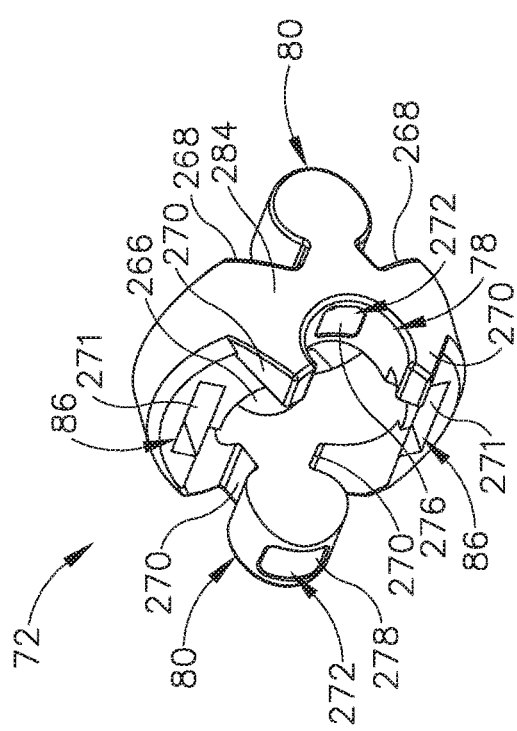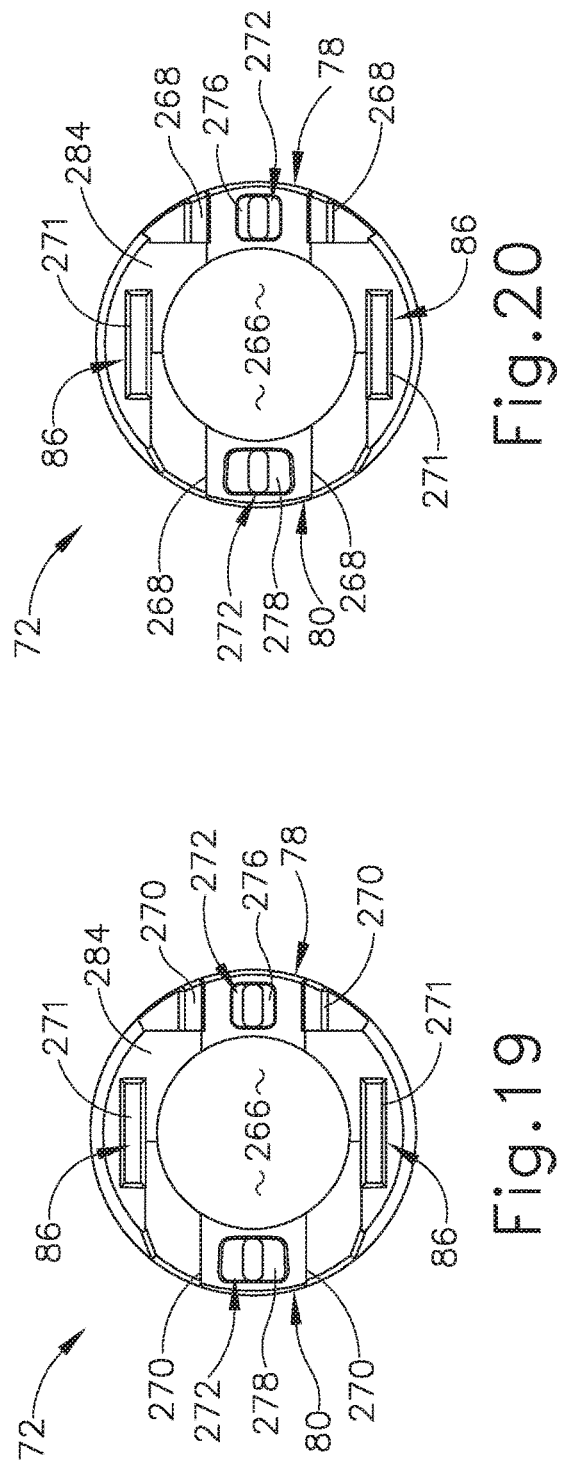

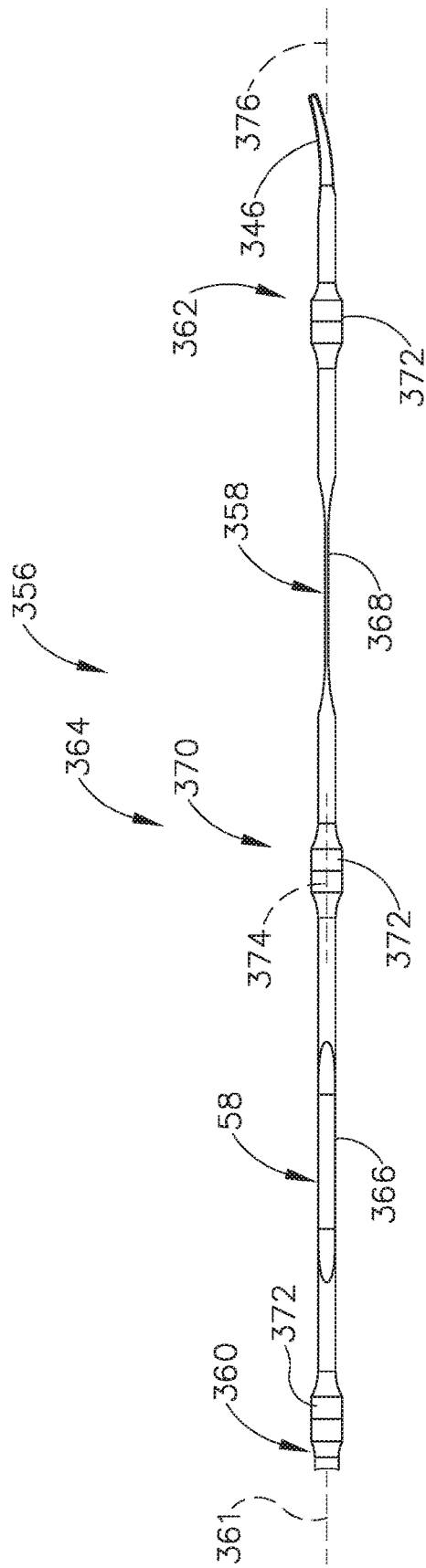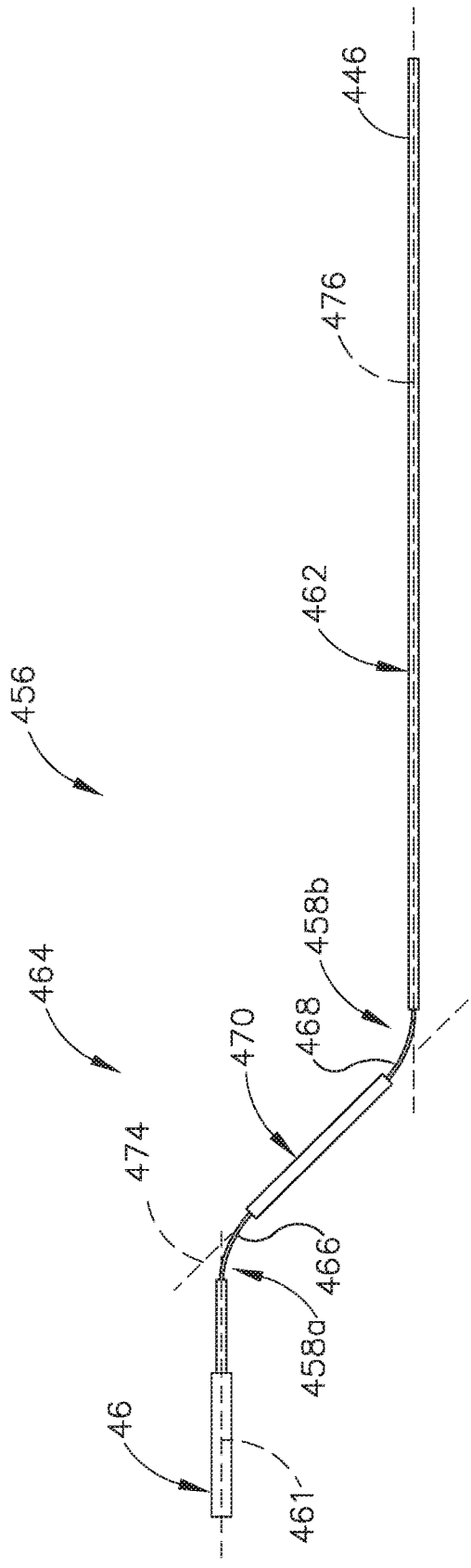

ULTRASONIC SURGICAL INSTRUMENT WITH A MULTI-PLANAR ARTICULATING SHAFT ASSEMBLY

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. The power level used to drive the blade element may be varied (e.g., in real time) based on sensed parameters such as tissue impedance, tissue temperature, tissue thickness, and/or other factors. Some instruments have a clamp arm and clamp pad for grasping tissue with the blade element.

Such surgical instruments may be directly gripped and manipulated by a surgeon or incorporated into a robotically assisted surgery. During robotically assisted surgery, the surgeon typically operates a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller typically includes one or more hand input devices (such as joysticks, exoskeletol gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a tissue grasper, a needle driver, an electrosurgical cautery probes, etc. Each of these structures performs functions for the surgeon, for example, cutting tissue, coagulating tissue, holding or driving a needle, grasping a blood vessel, dissecting tissue, or cauterizing tissue.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein; and U.S. Pat. No. 8,911,460, entitled "Ultrasonic Surgical Instruments," issued Dec. 16, 2014, the disclosure of which is incorporated by reference herein; and U.S. Pat. No. 9,023,071, entitled "Ultrasonic Device for Fingertip Control," issued May 5, 2015, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; U.S. Pub. No. 2008/0200940, entitled "Ultrasonic Device for Cutting and Coagulating," published Aug. 21, 2008, the disclosure of which is incorporated by reference herein; and U.S. Pat. No. 9,023,071, entitled "Ultrasonic Device for Fingertip Control," issued May 5, 2015, the disclosure of which is incorporated by reference herein.

Some ultrasonic surgical instruments may include a cordless transducer such as that disclosed in U.S. Pat. No. 9,381,058, entitled "Recharge System for Medical Devices," issued Jul. 5, 2016, the disclosure of which is incorporated by reference herein; U.S. Pub. No. 2012/0116265, entitled "Surgical Instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pat. No. 9,393,037, issued Jul. 19, 2016, entitled "Surgical Instruments with Articulating Shafts," the disclosure of which is incorporated by reference herein; U.S. Pat. No. 9,095,367, issued Aug. 4, 2015, entitled "Flexible Harmonic Waveguides/Blades for Surgical Instruments," the disclosure of which is incorporated by reference herein; U.S. Pat. No. 10,226,274, issued Mar. 12, 2019, entitled "Ultrasonic Surgical Instrument with Articulation Joint Having Plurality of Locking Positions," the disclosure of which is incorporated by reference herein; U.S. Pat. No. 10,034,683, entitled "Ultrasonic Surgical Instrument with Rigidizing Articulation Drive Members," issued Jul. 31, 2018, the disclosure of which is incorporated by reference herein; U.S. Pat. Pub. No. 2016/0302818, published Oct. 10, 2016, entitled "Ultrasonic Surgical Instrument with Movable Rigidizing Member," the disclosure of which is incorporated by reference herein; U.S. Pat. Pub. No. 2016/0302819, published Oct. 20, 2016, entitled "Ultrasonic Surgical Instrument with Articulating End Effector having a Curved Blade," the disclosure of which is incorporated by reference herein; U.S. Pat. No. 10,342,567, issued Jul. 9, 2019, entitled "Ultrasonic Surgical Instrument with Opposing Thread Drive for End Effector Articulation," the disclosure of which is incorporated by reference herein; U.S. Pat. Pub. No. 2015/0320438, published Nov. 12, 2015, entitled "Ultrasonic Surgical Instrument with End Effector Having Restricted Articulation," the disclosure of which is incorporated by reference herein; U.S. Pat. Pub. No. 2017/0281217, published Oct. 5, 2017, entitled "Surgical Instrument with Dual Mode Articulation Drive," the disclosure of which is incorporated by reference herein; U.S. Pat. Pub. No. 2017/0281218, published Oct. 5, 2017, entitled "Surgical Instrument with Motorized Articulation Drive in Shaft Rotation Knob," the disclosure of which is incorporated by reference herein; U.S. Pat. Pub. No. 2017/0281219, published Oct. 5, 2017, entitled "Surgical Instrument with Locking Articulation Drive Wheel," the disclosure of which is incorporated by reference herein; U.S. Pat. Pub. No. 2017/0281220, published Oct. 5, 2017, entitled "Surgical Instrument with Selectively Locked Articulation Assembly," the disclosure of which is incorporated by reference herein; and U.S. Pat. Pub. No. 2017/0281221, published Oct. 5, 2017, entitled "Articulation Joint for Surgical Instrument," the disclosure of which is incorporated by reference herein.

Some instruments are operable to seal tissue by applying radiofrequency (RF) electrosurgical energy to the tissue. An example of a surgical instrument that is operable to seal tissue by applying RF energy to the tissue is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Some instruments are capable of applying both ultrasonic energy and RF electrosurgical energy to tissue. Examples of such instruments are described in U.S. Pat. No. 9,949,785, entitled "Ultrasonic Surgical Instrument with Electrosurgical Feature," issued Apr. 24, 2018, the disclosure of which is incorporated by reference herein; and U.S. Pat. No. 8,663,220, entitled "Ultrasonic Surgical Instruments," issued Mar. 4, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 17 depicts a rear, distal perspective view of an intermediate link of the proximal articulation section of FIG. 8;

FIG. 18 depicts a rear, proximal perspective view of the intermediate link of FIG. 17;

FIG. 19 depicts a distal end elevational view of the intermediate link of FIG. 17;

FIG. 20 depicts a proximal end elevational view of the intermediate link of FIG. 17;

FIG. 26 depicts a top view of the acoustic waveguide of FIG. 25 in the straight contour;

FIG. 27 depicts a top view of a second exemplary multi-flex acoustic waveguide with a flexible distal yaw ribbon and a flexible proximal pitch ribbon in an exemplary dual arcuate contour;

Figure 1:
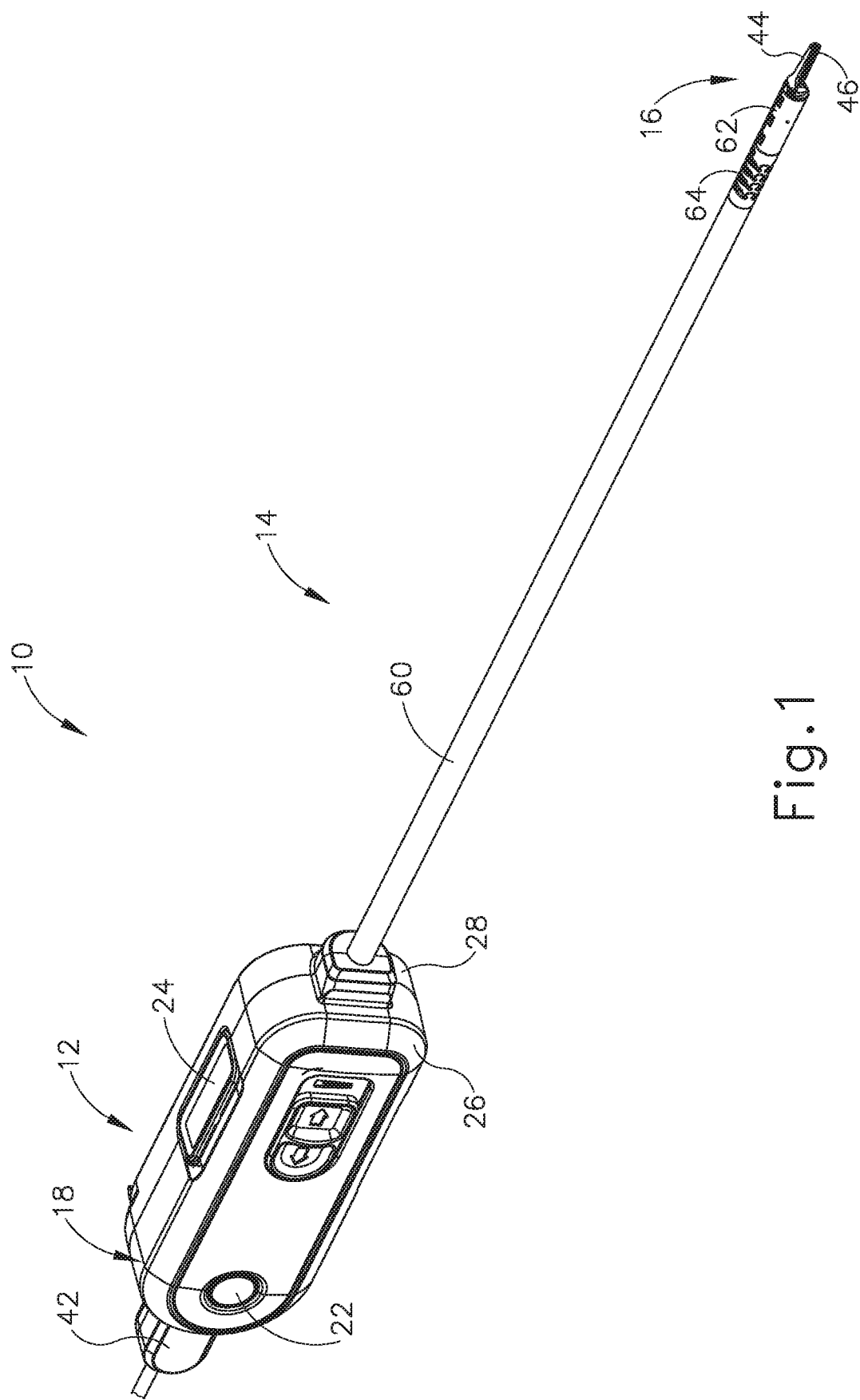
FIG. 1 depicts a front perspective view of a first example of an ultrasonic surgical instrument having an end effector, a base assembly configured to connect to a robotic driven interface, and a first exemplary shaft assembly with a first exemplary acoustic waveguide.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "front," "rear," "clockwise," "counterclockwise," "longitudinal," and "transverse" also are used herein for reference to relative positions and directions. Such terms are used below with reference to views as illustrated for clarity and are not intended to limit the invention described herein.

I. Exemplary Surgical Instrument

FIG. 1 shows an exemplary surgical instrument, such as an ultrasonic surgical instrument (10). At least part of ultrasonic surgical instrument (10) may be constructed and operable in accordance with at least some of the teachings of any of the various patents, patent application publications, and patent applications that are cited herein. As described therein and as will be described in greater detail below, ultrasonic surgical instrument (10) is operable to cut tissue and seal or weld tissue (e.g., a blood vessel, etc.) substantially simultaneously. While the present example incorporates various ultrasonic features as ultrasonic surgical instrument (10), the invention is not intended to be unnecessarily limited to the ultrasonic features described herein.

Ultrasonic surgical instrument (10) of the present example comprises a body assembly, such as a base assembly (12), a shaft assembly (14), and an end effector (16). Base assembly (12) includes a housing (18), a button (22), and a pair of latch clasps (24). Button (22) is operatively connected to an electrical base power controller (not shown) and configured to selectively power ultrasonic surgical instrument (10) for use. In addition, housing (18) of the present example includes a front housing cover (26) and a rear housing cover (28) removably secured together via latch clasps (24). More particularly, latch clasps (24) removably secure front housing cover (26) to rear housing cover (28) such that front housing cover (26) may be removed for accessing an interior space (30) (see FIG. 5) within base assembly (12). Shaft assembly (14) distally extends from base assembly (12) to end effector (16) to thereby communicate mechanical and/or electrical forces therebetween for use as will be discussed below in greater detail. As shown in the present example, base assembly (12) is configured to operatively connect to a robotic drive (not shown) for driving various features of shaft assembly (14) and/or end effector (16). However, in another example, body assembly may alternatively include a handle assembly (not shown), which may include a pistol grip (not shown) in one example, configured to be directly gripped and manipulated by the surgeon for driving various features of shaft assembly (14) and/or end effector (16). The invention is thus not intended to be unnecessarily limited to use with base assembly (12) and the robotic drive (not shown).

Figure 2:
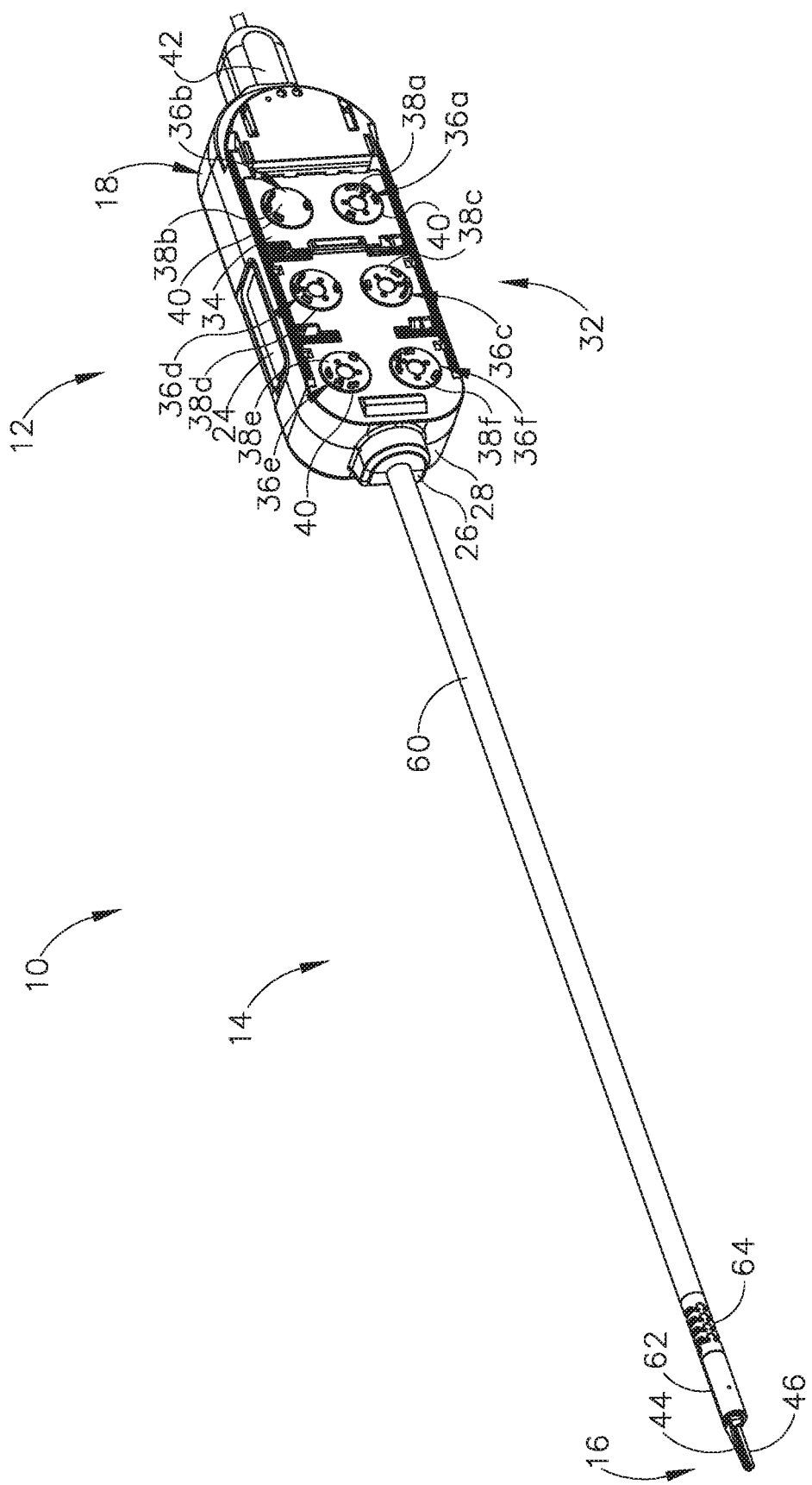
FIG. 2 depicts a rear perspective view of the ultrasonic surgical instrument of FIG. 1.

To this end, with respect to FIG. 2, base assembly (12) includes a robotic driven interface (32) extending through a base plate (34) of rear housing cover (28) and configured to mechanically couple with the robotic drive (not shown). Robotic driven interface (32) of the present example includes a plurality of instrument actuators (36a, 36b, 36c, 36d, 36e, 360) having a plurality of input bodies (38a, 38b, 38c, 38d, 38e, 38f), respectively. Each input body (38a, 38b, 38c, 38d, 38e, 380), which may also be referred to herein as a "puck," is configured to removably connect with the robotic drive (not shown) and, in the present example, is generally cylindrical and rotatable about an axis. Input bodies (38a, 38b, 38c, 38d, 38e, 380) have a plurality of slots (40) configured to receive portions of the robotic drive (not shown) for gripping and rotatably driving input bodies (38a, 38b, 38c, 38d, 38e, 380) in order to direct operation of shaft assembly (14) and/or end effector (16) as will be discussed below in greater detail. Base assembly (12) also receives an electrical plug (42) operatively connected to an electrical power source (not shown) to provide electrical power to base assembly (12) for operation as desired, such as powering electrical base power controller (not shown) and directing electrical energy to various features of shaft assembly (14) or end effector (16) associated with cutting, sealing, or welding tissue.

A. Exemplary End Effector and Acoustic Drivetrain

Figure 3A:
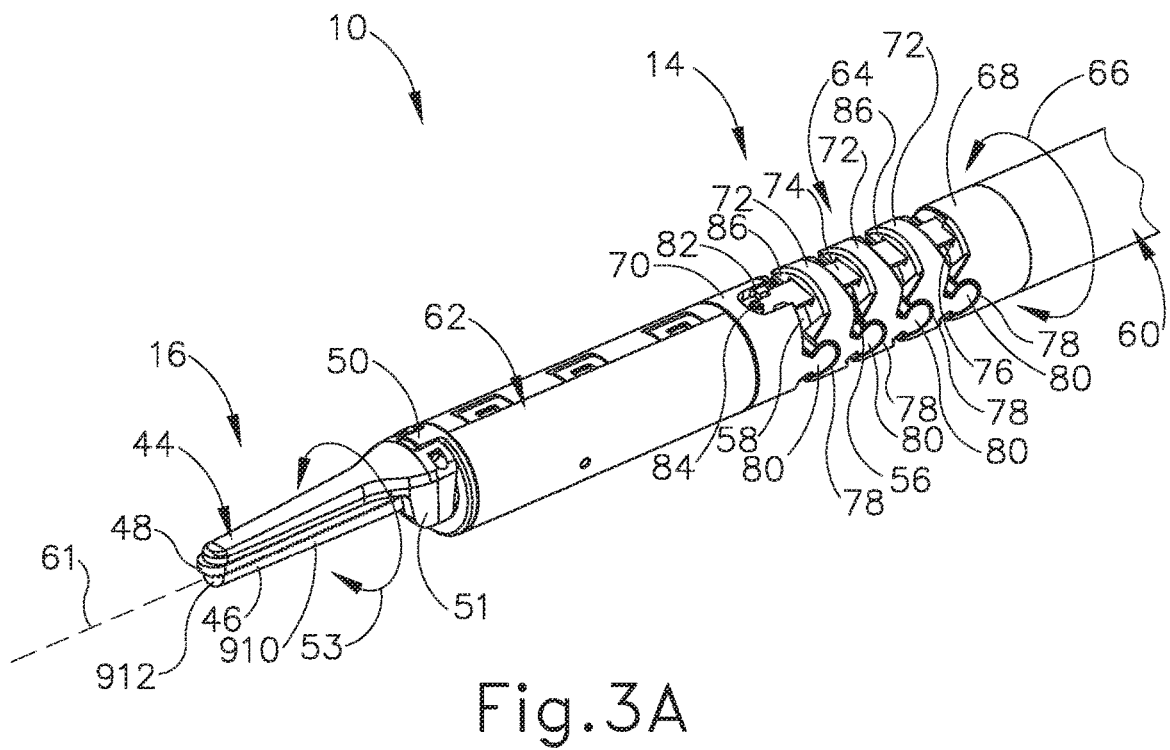
FIG. 3A depicts an enlarged perspective view of the ultrasonic surgical instrument of FIG. 1 with the end effector in a closed position and the shaft assembly in a straight configuration.
Figure 3B:
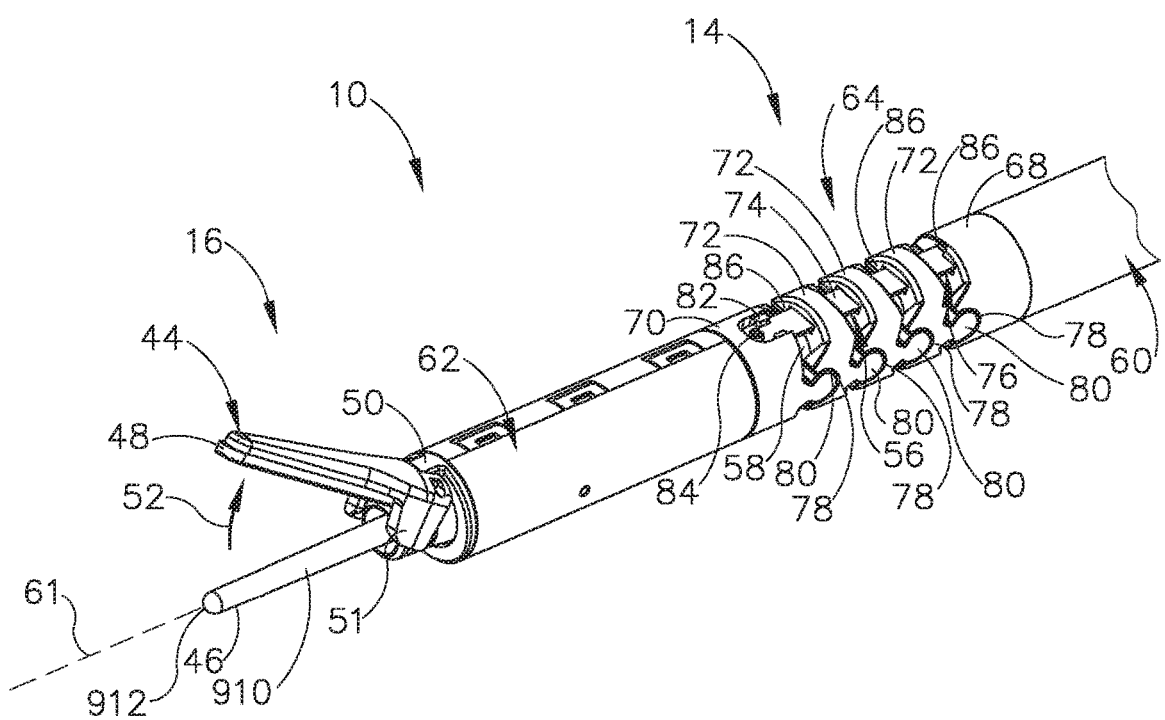
FIG. 3B depicts the enlarged perspective view of the ultrasonic surgical instrument similar to FIG. 3A, but showing the end effector in an open position.

As best seen in FIGS. 3A-3B, end effector (16) of the present example includes a clamp arm (44) and an ultrasonic blade (46). Clamp arm (44) has a clamp pad (48) secured to an underside of clamp arm (44), facing blade (46). In one example, clamp pad (48) may comprise polytetrafluoroethylene (PTFE) and/or any other suitable material(s). Clamp arm (44) is pivotally secured to a distally projecting tongue (50) of shaft assembly (14). Clamp arm (44) is operable to selectively pivot toward and away from blade (46) to selectively clamp tissue between clamp arm (44) and blade (46). A pair of arms (51) extend transversely from clamp arm (44) and are pivotally secured to another portion of shaft assembly (14) configured to longitudinally slide to pivot clamp arm (44) as indicated by an arrow (52) between a closed position shown in FIG. 3A and an open position shown in FIG. 3B.

In addition to pivoting relative to blade (46), clamp arm (44) of the present example is further configured to rotate about blade (46) relative to blade (46) and also relative to shaft assembly (14) as indicated by an arrow (53). In one example, clamp arm (44) rotates in the clockwise or counterclockwise directions completely around blade (46) and may be selectively fixed in any angular position relative to blade (46) for directing clamp arm (44) from the open position to the closed position for clamping tissue. In another example, clamp arm (44) may have rotational stops (not shown) configured to limit rotational movement of clamp arm (44) relative to blade (46) in one or more predetermined positions.

Blade (46) of the present example is operable to vibrate at ultrasonic frequencies in order to effectively cut through and seal tissue, particularly when the tissue is being compressed between clamp pad (48) and blade (46). Blade (46) is positioned at a distal end of an acoustic drivetrain. This acoustic drivetrain includes a transducer assembly (54) (see FIG. 5) and an acoustic waveguide (56), which includes a flexible portion (58) discussed below in greater detail. It should be understood that waveguide (56) may be configured to amplify mechanical vibrations transmitted through waveguide (56). Furthermore, waveguide (56) may include features operable to control the gain of the longitudinal vibrations along waveguide (56) and/or features to tune waveguide (56) to the resonant frequency of the system. Various suitable ways in which waveguide (56) may be mechanically and acoustically coupled with transducer assembly (54) (see FIG. 5) will be apparent to those of ordinary skill in the art in view of the teachings herein.

Those of ordinary skill in the art will understand that, as a matter of physics, a distal end of blade (46) is located at a position corresponding to an antinode associated with resonant ultrasonic vibrations communicated through flexible portion (58) of waveguide (56). When transducer assembly (54) (see FIG. 5) is energized, the distal end of blade (46) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (54) (see FIG. 5) of the present example is activated, these mechanical oscillations are transmitted through waveguide (56) to reach blade (46), thereby providing oscillation of blade (46) at the resonant ultrasonic frequency. Thus, when tissue is secured between blade (46) and clamp pad (48), the ultrasonic oscillation of blade (46) may simultaneously sever the tissue and denature the proteins in adjacent tissue cells, thereby providing a coagulative effect with relatively little thermal spread. In some versions, end effector (16) is operable to apply radiofrequency (RF) electrosurgical energy to tissue in addition to applying ultrasonic energy to tissue. In any case, other suitable configurations for an acoustic transmission assembly and transducer assembly (54) will be apparent to one of ordinary skill in the art in view of the teachings herein. Similarly, other suitable configurations for end effector (16) will be apparent to those of ordinary skill in the art in view of the teachings herein.

B. Exemplary Shaft Assembly and Articulation Section

As shown in FIGS. 3A-3B, shaft assembly (14) includes a proximal shaft portion (60) extending along a longitudinal axis (61), a distal shaft portion (62) distally projecting relative to the proximal shaft portion (60), and an articulation section (64) extending between proximal and distal shaft portions (60, 62). Shaft assembly (14) is configured to rotate about longitudinal axis (61) as indicated by an arrow (66). In one example, shaft assembly (14) rotates in the clockwise or counterclockwise directions completely around longitudinal axis (61) and may be selectively fixed in any rotational position about longitudinal axis (61) for positioning articulation section (64) and/or end effector (16) about longitudinal axis (61). While end effector (16) generally rotates with shaft assembly (14) as indicated by arrow (66), end effector (16) may be simultaneously and independently rotated as indicated by arrow (53) relative to shaft assembly (14) during use for repositioning portions of shaft assembly (14) and/or end effector (16) as desired.

Articulation section (64) is configured to selectively position end effector (16) at various lateral deflection angles relative to longitudinal axis (61) defined by proximal shaft portion (60). Articulation section (64) may take a variety of forms. In the present example, articulation section (64) includes a proximal link (68), a distal link (70), and a plurality of intermediate links (72) connected in series between proximal and distal links (68, 70). Articulation section (64) further includes a pair of articulation bands (74) extending along a pair of respective channels (76) collectively defined through links (68, 70, 72). Links (68, 70, 72) are generally configured to pivot relative to each other upon actuation of articulation bands (74) to thereby bend articulation section (64) with flexible portion (58) of waveguide (56) therein to achieve an articulated state. By way of example only, articulation section (64) may alternatively or additionally be configured in accordance with one or more teachings of U.S. Pat. No. 9,402,682, entitled "Articulation Joint Features for Articulating Surgical Device," issued Aug. 2, 2016, the disclosure of which is incorporated by reference herein. As another merely illustrative example, articulation section (64) may alternatively or additionally be configured in accordance with one or more teachings of U.S. Pat. No. 9,393,037, issued Jul. 19, 2016, entitled "Surgical Instruments with Articulating Shafts," the disclosure of which is incorporated by reference herein and U.S. Pat. No. 9,095,367, issued Aug. 4, 2015, entitled "Flexible Harmonic Waveguides/Blades for Surgical Instruments," the disclosure of which is incorporated by reference herein. In addition to or in lieu of the foregoing, articulation section (64) and/or may be constructed and/or operable in accordance with at least some of the teachings of U.S. Pat. No. 10,034,683, entitled "Ultrasonic Surgical Instrument with Rigidizing Articulation Drive Members," issued on Jul. 31, 2018. Alternatively, articulation section (64) may be constructed and/or operable in any other suitable fashion.

Links (68, 70, 72) shown in FIGS. 3B-4B pivotally interlock to secure distal shaft portion (62) relative to proximal shaft portion (60) while allowing for deflection of distal shaft portion (62) relative to longitudinal axis (61). In the present example, proximal link (68) is rigidly connected to proximal shaft portion (60) and has a pair of arcuate grooves (78) opposed from each other. Intermediate links (72) respectively have a pair of arcuate tongues (80) proximally extending therefrom and a pair of arcuate grooves (78) positioned distally opposite from respective tongues (80).

Each intermediate link (72) has tongues (80) pivotally received within adjacent arcuate grooves (78) of another intermediate link (72) or proximal link (68) as applicable. Distal link (70) is rigidly connected to distal shaft portion (62) and has another pair of arcuate tongues (80) opposed from each other and pivotally received within adjacent arcuate grooves (78) of intermediate link (72). Tongues (80) and grooves (78) connect together to form the series of interlocked links (68, 70, 72).

Figure 4A:
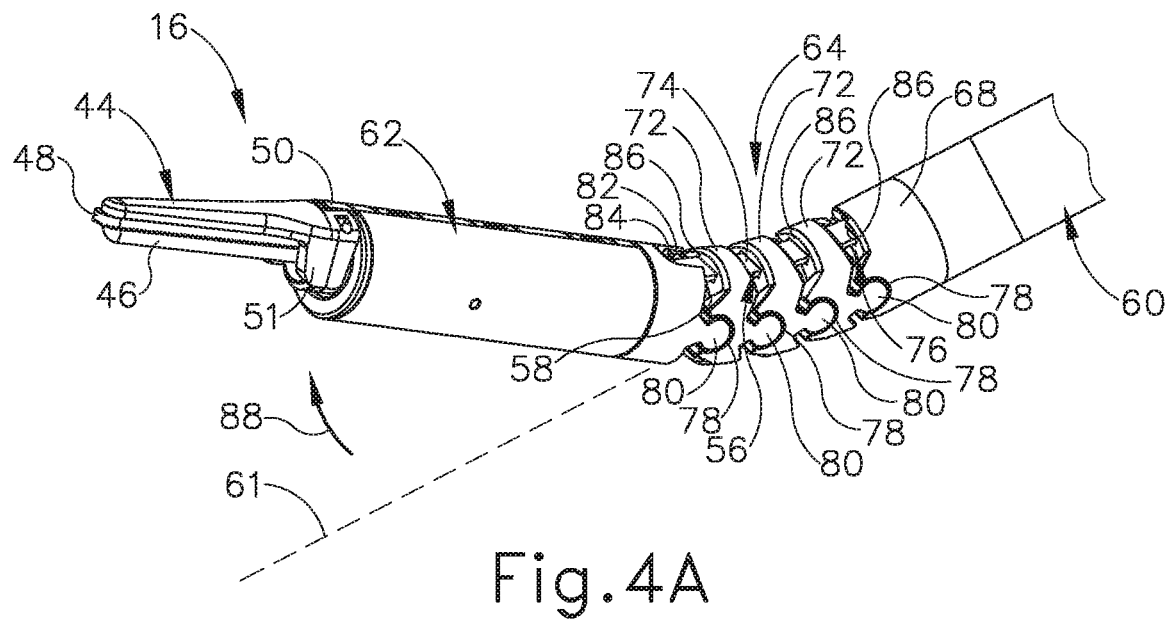
FIG. 4A depicts an enlarged perspective view of the ultrasonic surgical instrument of FIG. 1 with the end effector in a closed position and the shaft assembly in a first articulated configuration.
Figure 4B:
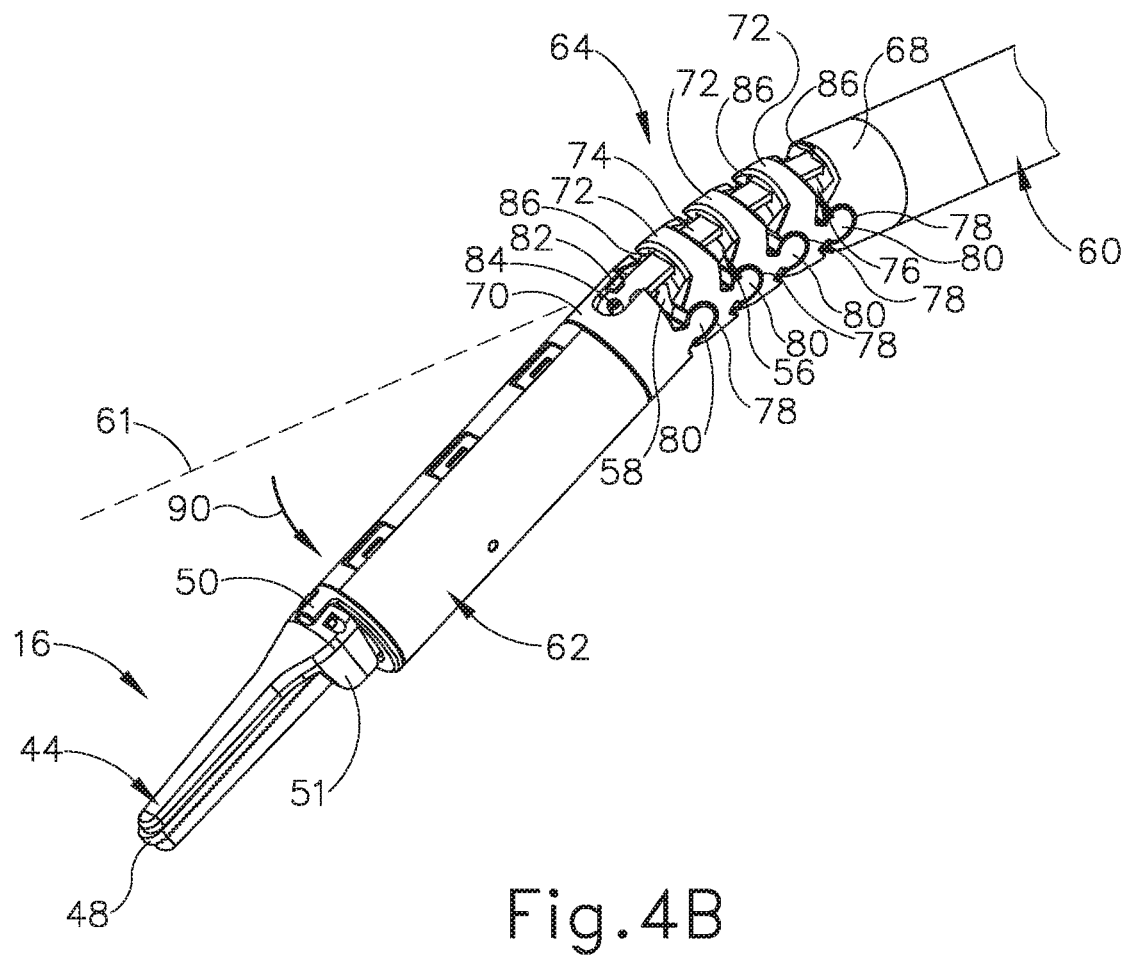
FIG. 4B depicts the enlarged perspective view of the ultrasonic surgical instrument similar to FIG. 4A, but with the shaft assembly in a second articulated configuration.

Distal link (70) further includes a pair of opposing notches (82) with a pin (84) therein configured to receive distal end portions of respective articulation bands (74). More particularly, pins (84) extend through a hole in each respective articulation bands (74) while distal end portions of respective articulation bands (74) are coupled within notches (82). Slots (86) in each of intermediate and proximal links (72, 68) longitudinally align with each other and notches (82) to collectively define channels (76) configured to receive articulation bands (74) while allowing articulation bands (74) to slide relative to links (68, 70, 72). To this end, when articulation bands (74) translate longitudinally in an opposing fashion, this will cause articulation section (64) to bend, thereby laterally deflecting end effector (16) away from the longitudinal axis (61) of proximal shaft portion (60) from a straight configuration as shown in FIG. 3B to a first articulated configuration as shown in FIG. 4A and indicated by an arrow (88) or a second articulated configuration as shown in FIG. 4B and indicated by an arrow (90). In particular, end effector (16) will be articulated toward the articulation band (74) that is being pulled proximally. During such articulation, the other articulation band (74) may be pulled distally. Alternatively, the other articulation band (74) may be driven distally by an articulation control. Furthermore, flexible acoustic waveguide (56) is configured to effectively communicate ultrasonic vibrations from waveguide (56) to blade (46) even when articulation section (64) is in an articulated configuration as shown in FIGS. 4A-4B.

C. Exemplary Base Assembly with Instrument Actuators for Robotic Interface

Figure 5:
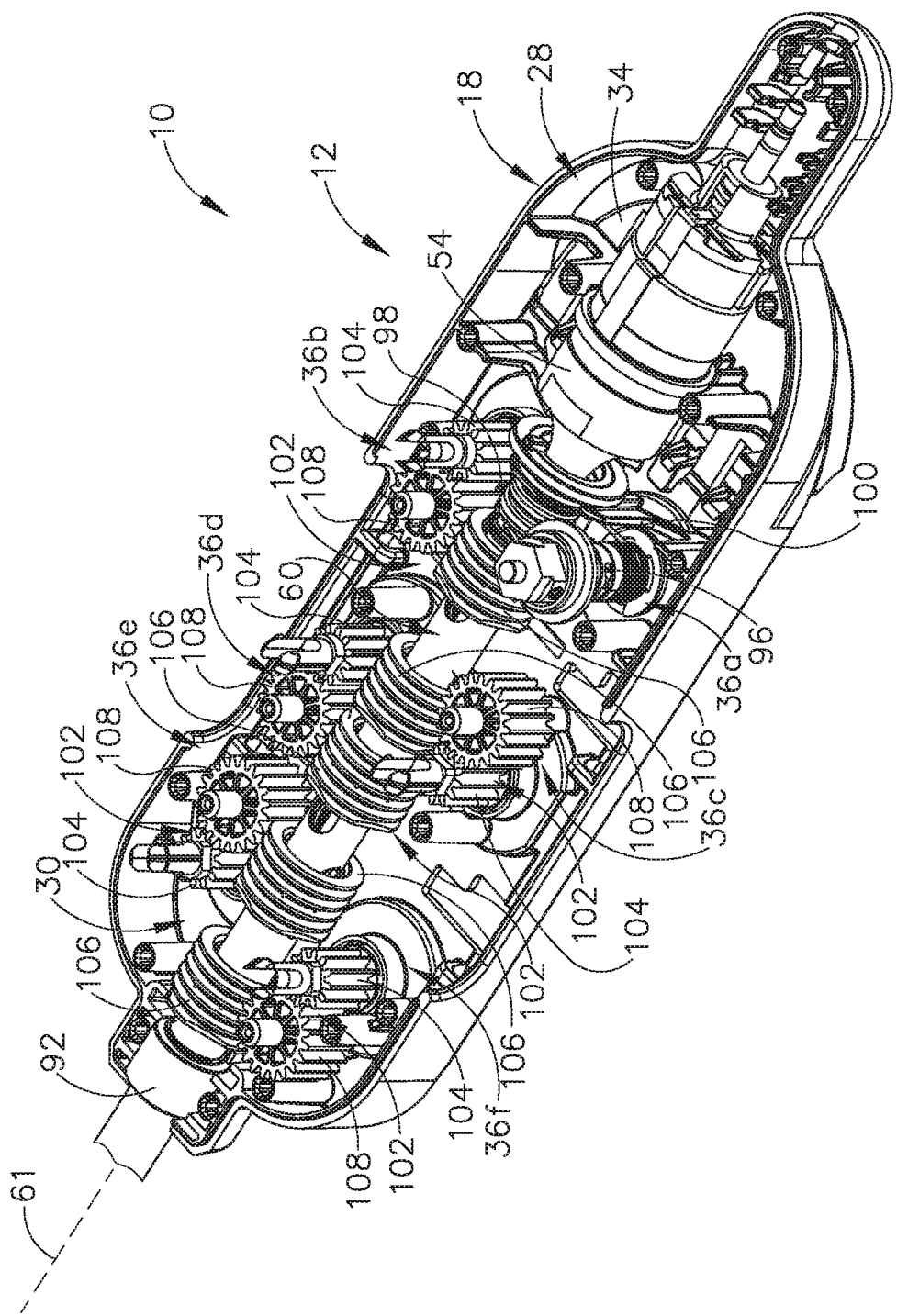
FIG. 5 depicts an enlarged perspective view of the ultrasonic surgical instrument of FIG. 1 with the base assembly having various components removed for greater clarity of an interior space of the base assembly.

FIG. 5 shows interior space (30) of base assembly (12) with instrument actuators (36a, 36b, 36c, 36d, 36e, 360 in greater detail. Generally, instrument actuators (36a, 36b, 36c, 36d, 36e, 360 are engaged with shaft assembly (14) and configured to direct movement of end effector (16) and/or shaft assembly (14), such as movement indicated above in one example by arrows (52, 53, 66, 88, 90) (see FIGS. 3A-4B). Shaft assembly (14) is received within base assembly (12) and supported by bearings (92) therein to operatively connect each respective instrument actuator (36a, 36b, 36c, 36d, 36e, 360 to shaft assembly (14) as well as operatively connect acoustic waveguide (56) (see FIG. 3A) to transducer assembly (54) and a generator (not shown) of the acoustic drivetrain. More particularly, transducer assembly (54) is coupled with generator (not shown) such that transducer assembly (54) receives electrical power from generator (not shown). Piezoelectric elements (not shown) in transducer assembly (54) convert that electrical power into ultrasonic vibrations. Generator (not shown) may be coupled to the electrical power source (not shown) via electrical plug (42) (see FIG. 1) and a control module (not shown) that are configured to provide a power profile to transducer assembly (54) that is particularly suited for the generation of ultrasonic vibrations through transducer assembly (54). By way of example only, generator (not shown) may comprise a GEN04 or GEN11 sold by Ethicon Endo-Surgery, Inc. of Cincinnati, Ohio. In addition or in the alternative, generator (not shown) may be constructed in accordance with at least some of the teachings of U.S. Pub. No. 2011/0087212, entitled "Surgical Generator for Ultrasonic and Electrosurgical Devices," published Apr. 14, 2011, the disclosure of which is incorporated by reference herein. Still other suitable forms that generator (not shown) may take, as well as various features and operabilities that generator (not shown) may provide, will be apparent to those of ordinary skill in the art in view of the teachings herein.

Figure 6:
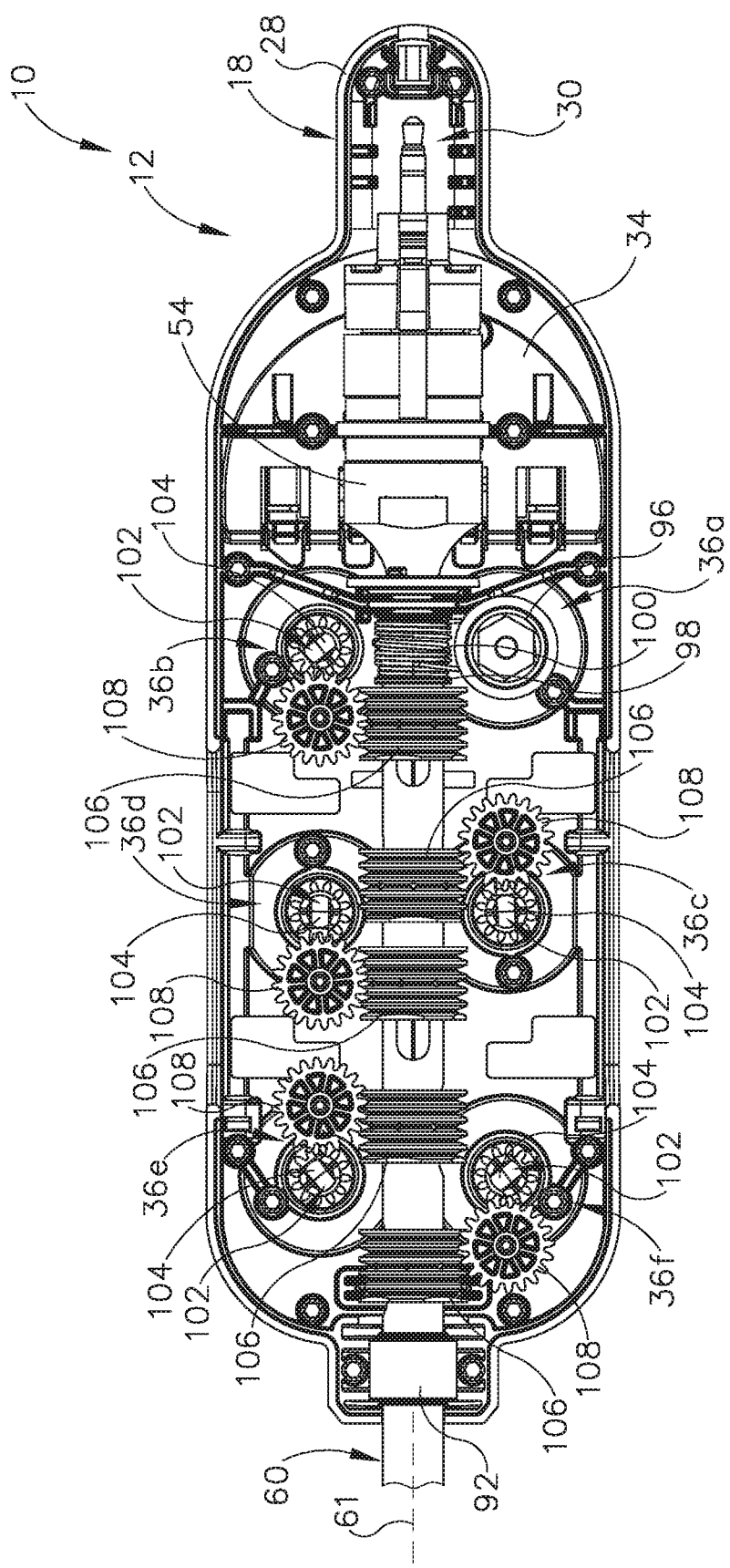
FIG. 6 depicts an enlarged front view of the ultrasonic surgical instrument of FIG. 1 with the base assembly having various components removed for greater clarity of the interior space of the base assembly.

The present example of base assembly (12) shown in FIGS. 5-6 includes six instrument actuators (36a, 36b, 36c, 36d, 36e, 360, although it will be appreciated that any such number of such instrument actuators (36a, 36b, 36c, 36d, 36e, 360 configured to direct movement of shaft assembly (14) and/or end effector (16) may be similarly used. As shown with respect to operation of ultrasonic surgical instrument (10), instrument actuator (36a) is more particularly a roll system actuator (36a) configured to rotate shaft assembly (14) about longitudinal axis (61). In contrast, instrument actuators (36b, 36c, 36d, 36e, 360 are linear system actuators (36b, 36c, 36d, 36e, 360 configured to translationally drive movement of portions of end effector (16) and/or shaft assembly (14) while simultaneously allowing for rotation of shaft assembly (14) via roll system actuator (36a).

Roll system actuator (36a) in one example includes a drive spool (96) rigidly connected to puck (38a) (see FIG. 2) and a driven spool (98) rigidly connected to proximal shaft portion (60) within housing (18). Drive spool (96) is mounted to rotate with puck (38a) (see FIG. 2) about a common puck axis, whereas driven spool (98) is mounted to rotate with proximal shaft portion (60) about the longitudinal axis (61). A cable (100) wraps around each of the drive and driven spools (96, 98), accommodating the differing orientation of the puck axis and longitudinal axis (61), such that rotating drive spool (96) via puck (38a) (see FIG. 2) urges rotation of driven spool (98). In turn, shaft assembly (14), including proximal and distal shaft portions (60, 62) rotates about longitudinal axis (61) as indicated by arrow (66) (see FIG. 3A), such as by robotically driven actuation of puck (38a) (see FIG. 2).

Linear system actuators (36b, 36c, 36d, 36e, 360 of the present example include a gear-rack mechanism (102) having a rotatable drive gear (104), a translatable rack gear (106), and an idler gear (108) connected therebetween. Drive gears (104) are respectively connected to and rigidly project from pucks (38b, 38c, 38d, 38e, 380 (see FIG. 2), whereas each rack gear (106) is connected to another portion of proximal shaft portion (60) directing movement of shaft assembly (14) and/or end effector (16) as discussed above. Each rack gear (106) is cylindrical and rigidly connected relative to proximal shaft portion (60) to rotate therewith. Rack gear (106) is thereby configured to rotate with shaft assembly (14) while remaining meshed with idler gear (108). Rotating respective pucks (38b, 38c, 38d, 38e, 380 (see FIG. 2) thus respectively rotates drive gears (104) and idler gears (108) to translate rack gears (106) as desired.

In the present example, with respect to FIGS. 2-4B and FIG. 6, linear system actuator (36b) has puck (38b) operatively connected to clamp arm (44) to direct movement of clamp arm (44) between the open and closed positions according to arrow (52). Linear system actuators (36c, 36d) have respective pucks (38c, 38d) operatively connected to clamp arm (44) to direct movement of clamp arm (44) around blade (46) in both the clockwise and counterclockwise directions according to arrow (53). In addition, linear system actuators (36e, 360 have respective pucks (38e, 380 operatively connected to articulation bands (74) to direct movement of articulation section (64) according to arrows (88, 90) for deflecting end effector (16) relative to longitudinal axis (61). Of course, in other examples, instrument actuators (36a, 36b, 36c, 36d, 36e, 36f) may be alternatively configured with more or less actuators (36a, 36b, 36c, 36d, 36e, 360 and/or more or less movement as desired. The invention is thus not intended to be unnecessarily limited to instrument actuators (36a, 36b, 36c, 36d, 36e, 360 or particular movements of shaft assembly (14) and/or end effector (16) as described in the present example.

II. Exemplary Multi-Planar Articulation of Shaft Assembly

In some instances, with respect to FIGS. 1-4B, it may be desirable to guide deflection of end effector (16) at least in part according to various properties and/or constraints associated with components passing through articulation section (64) during use. By way of example, greater variability in such deflection, such as by increased articulation along shaft assembly (14), may increase strain on one or more flexible components within articulation section (64). Articulation section (64) may thus be desirably articulated via links (68, 70, 72) in one example to accurately and precisely guide movement of flexible components within articulation section (64) while reducing strain that may otherwise occur through these flexible components, such as acoustic waveguide (56).

Figure 7:
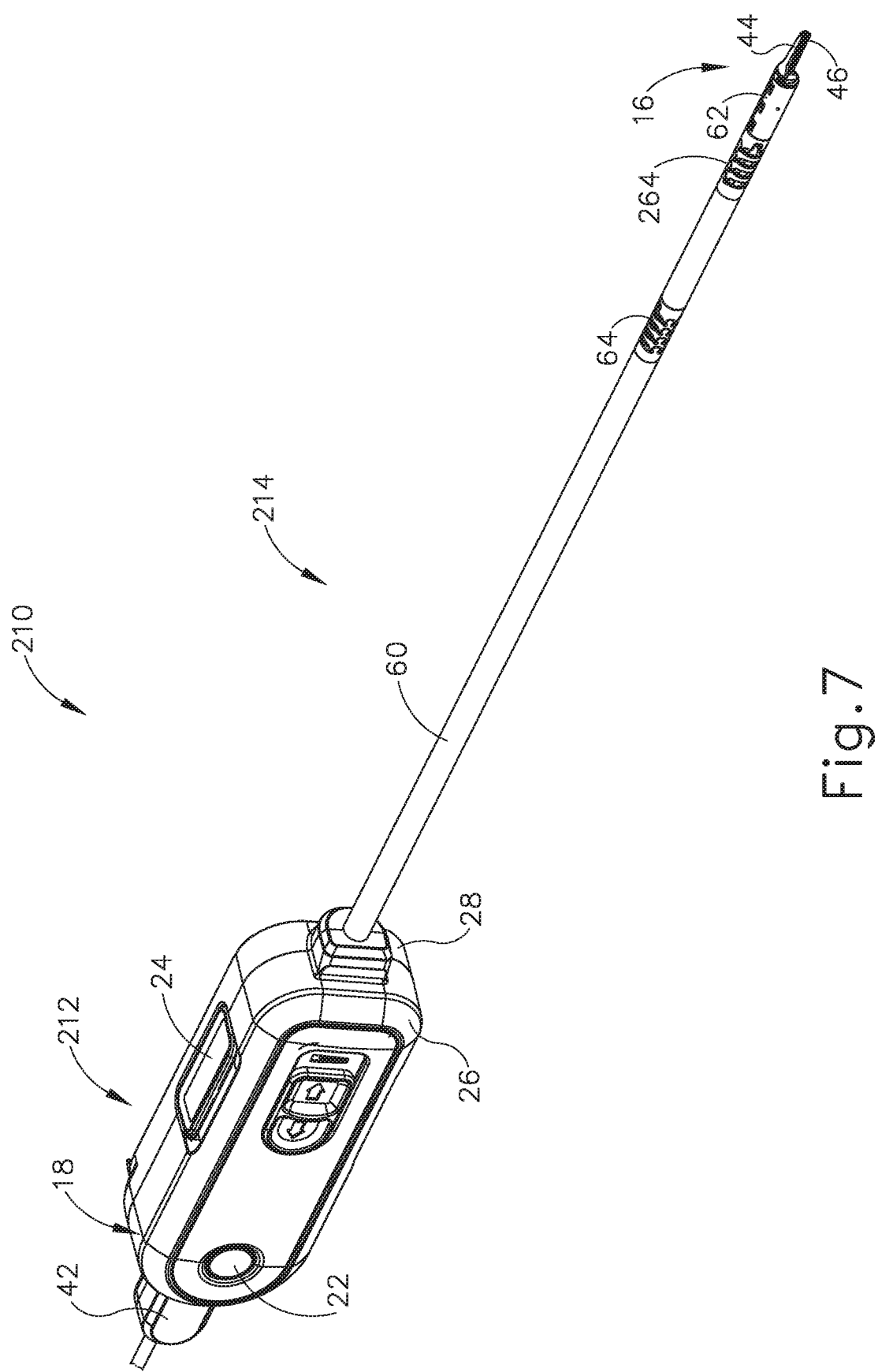
FIG. 7 depicts a front perspective view of a second example of an ultrasonic surgical instrument having a multi-planar shaft assembly in a straight configuration.
Figure 8:
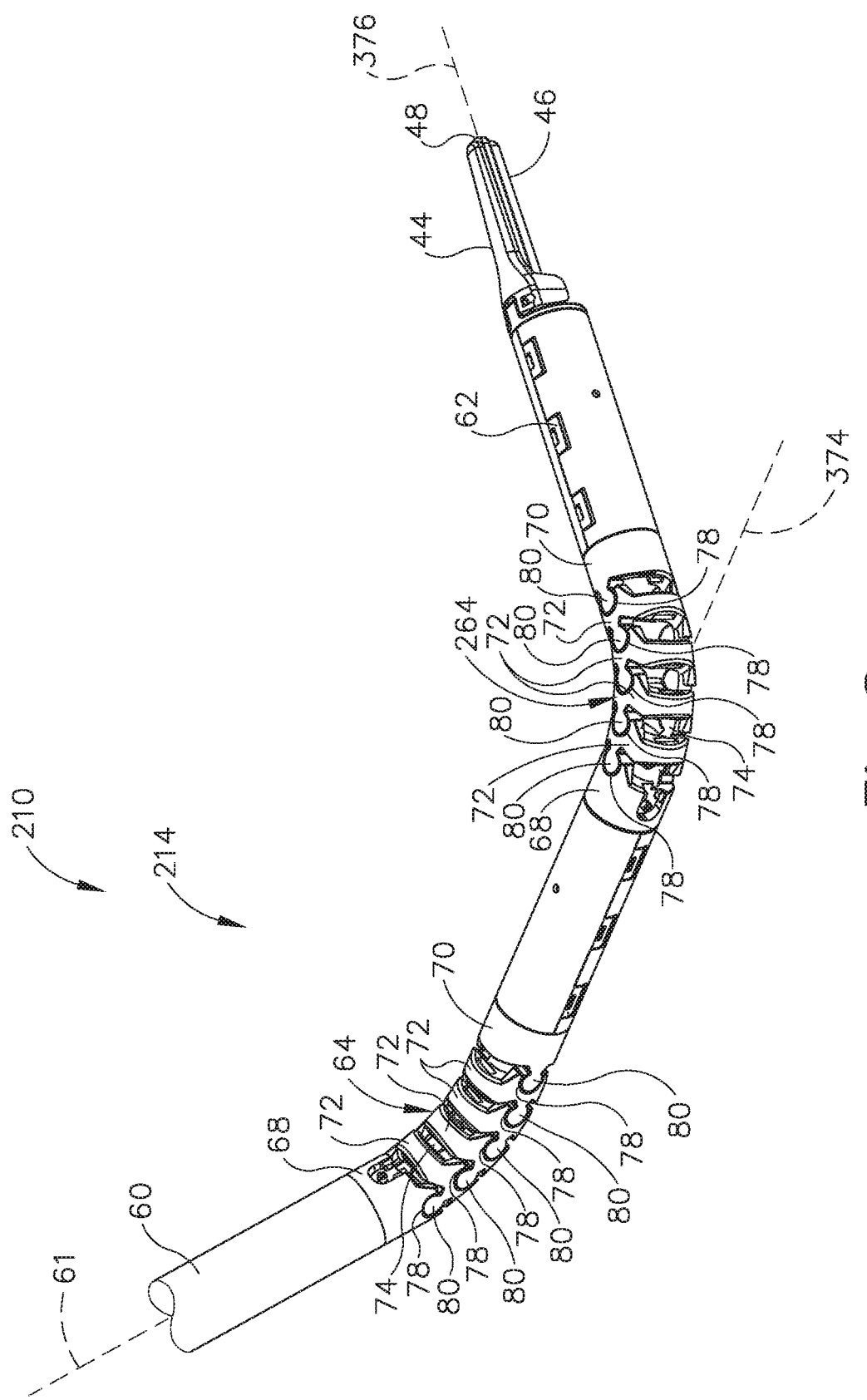
FIG. 8 depicts an enlarged, front perspective view of the shaft assembly of FIG. 7 with a distal articulation section and a proximal articulation section respectively in a distal articulated configuration and a proximal articulated configuration.
Figure 9:
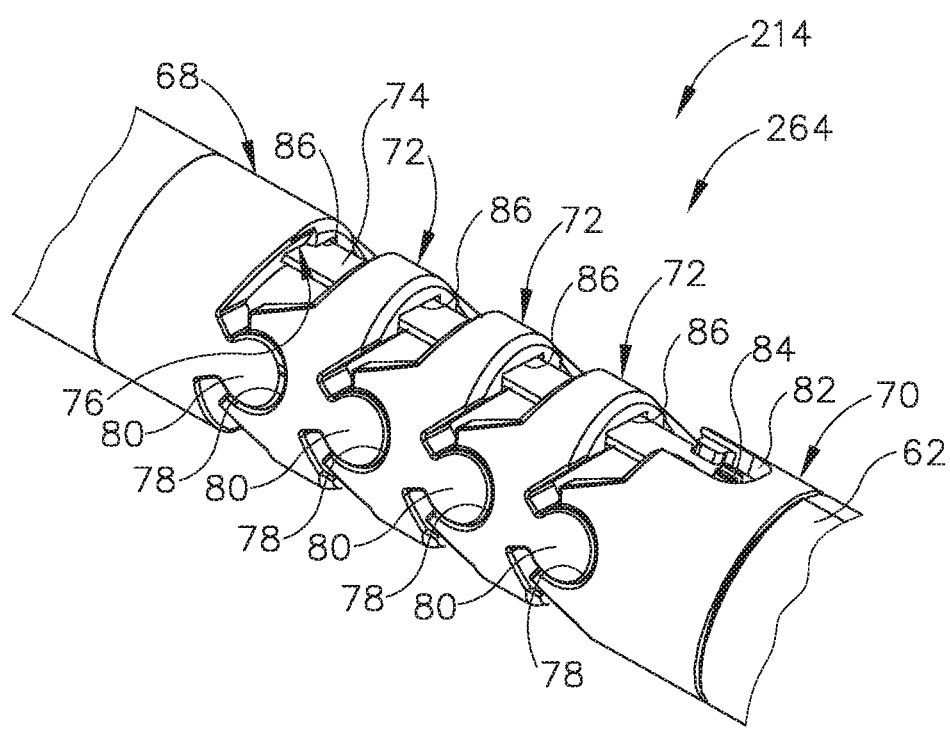
FIG. 9 depicts an enlarged, rear perspective view of the distal articulation section of FIG. 8 in the straight configuration.

By way of further example, greater variability of deflection along shaft assembly (14) may incorporate a plurality of articulation sections (64) with respective links (68, 70, 72) for guiding any one of a plurality of acoustic waveguides (356, 456, 556, 656, 756, 856) (see FIGS. 25-35B) through greater degrees of freedom than acoustic waveguide (56) of ultrasonic surgical instrument (10). To this end, shaft assembly (14) with end effector (16) is more generally configured to move longitudinally along longitudinal axis (61), laterally perpendicular to longitudinal axis (61), and transversely perpendicular to longitudinal axis (61) as well as rotate end effector (16) about longitudinal axis (61) and pivot end effector (16) along a plane, which may be pitch or yaw depending on the relative position of end effector (16). While such movement provides five degrees of freedom to end effector (16) via acoustic waveguide (56) during use, any one or more of the plurality of acoustic waveguides (356, 456, 556, 656, 756, 856) (see FIGS. 25-35B) described below are configured to enable end effector (16) to pivot through an additional plane for six degrees of freedom. Additional articulation sections (64) and/or alternative articulations (not shown) are thus configured to guide deflection of end effector (16) while reducing strain on acoustic waveguides (356, 456, 556, 656, 756, 856) (see FIGS. 25-35B). While the following provides additional details with respect to a second example of an ultrasonic surgical instrument (210) having dual articulation sections (64, 164) as shown in FIGS. 7-8, the invention is not intended to be unnecessarily limited to one or more of such articulation sections (64, 164). Indeed, any alternative articulation section (not shown) may be used alone or in combination for supporting acoustic waveguides having one or more flexible portions, such as acoustic waveguides (356, 456, 556, 656, 756, 856) (see FIGS. 25-35B) described below in greater detail. In addition, like numbers below indicate like features described above in greater detail.

A. Articulation Section for Multi-Planar Articulation

FIGS. 7-8 show a second example of an ultrasonic surgical instrument (210) having another example of a base assembly (212) and a distally extending multi-planar shaft assembly (214) with end effector (16). Base and shaft assemblies (212, 214) are similar to base and shaft assemblies (12, 14) (see FIG. 1) discussed above in greater detail, but are collectively configured for multi-planar articulation. More particularly, shaft assembly (214) includes articulation section (64) as a proximal articulation section (64) and further includes a distal articulation section (264). Base assembly (212) is thus configured to direct articulation of proximal articulation section (64) as discussed above with respect to base assembly (12) (see FIG. 1) and also configured to direct articulation of distal articulation section (264). Such movement of distal articulation section (264) in one example is performed by an additional instrument actuator (not shown). Alternatively, movement of distal articulation section (64) in another example is performed by another one of instrument actuators (36a, 36b, 36c, 36d, 36e, 36f). Unless explicitly stated herein, base and shaft assemblies (212, 214) are otherwise constructed and operable as base and shaft assemblies (12, 14) (see FIG. 1) discussed above in greater detail.

Proximal and distal articulation sections (64, 264) are similarly constructed in the present example with links (68, 70, 72) as discussed above. Proximal articulation section (64) thus articulates through a plane, whereas distal articulation section (264) articulates through another plane. In the present example, these planes are perpendicular to each other. Given the rotational orientation of shaft assembly (214) as shown in FIGS. 7-8, proximal articulation section (64) articulates through a pitch plane and distal articulation section (264) articulates through a yaw plane relative to clamp arm (44). However, it will be appreciated that such planes change relative to clamp arm (44) and/or as oriented in FIGS. 7-8, such as the invention is not intended to be unnecessarily limited to the yaw and pitch planes as shown in the present example. While FIG. 8 shows one example of dual articulation for each of proximal and distal articulation sections (64, 264) such that end effector (16) may be selectively moved according to six degrees of freedom, it will be further appreciated that any desired articulation and combination of respective articulations may be similarly used. Again, the invention is not intended to be unnecessarily limited to the particular angles of articulation shown in the yaw and pitch planes of the present example.

FIGS. 9-12 show distal articulation section (264) with proximal, distal, and intermediate links (68, 70, 72), articulation bands (74), and a distal flexible portion (358) of a first exemplary multi-flex acoustic waveguide (356) extending therethrough. Links (68, 70, 72) collectively define channels (76) configured to receive articulation bands (74) such that articulation bands (74) transversely align links (68, 70, 72) with a remainder of shaft assembly (214) as well as provide transverse support of links (68, 70, 72) along distal articulation section (264). As discussed above, links (68, 70, 72) have arcuate grooves (78) receiving arcuate tongues (80) along a lateral centerline positioned between articulation bands (74) such that articulation bands (74) are transversely offset and on opposing sides of distal flexible portion (358) thereby maintaining axial position of distal articulation section (264). Furthermore, each link (68, 70, 72) defines a link hollow (266) configured to receive distal flexible portion (358) and provide distal flexible portion (358) with sufficient and constant clearance space therealong to remain untouched by any portion of one of links (68, 70, 72) whether in the straight configuration or any articulated configuration, which is limited to maximum articulated configurations via cooperating distal and proximal stops (268, 270). To this end, proximal stop (270) on one link (68, 70, 72) is configured to engage distal stop (268) on another adjacent link (68, 70, 72) to thereby limit collective articulation of distal articulation section (264) and, in turn, limit strain due to articulation on distal flexible portion (358) of acoustic waveguide (356).

Figure 10:
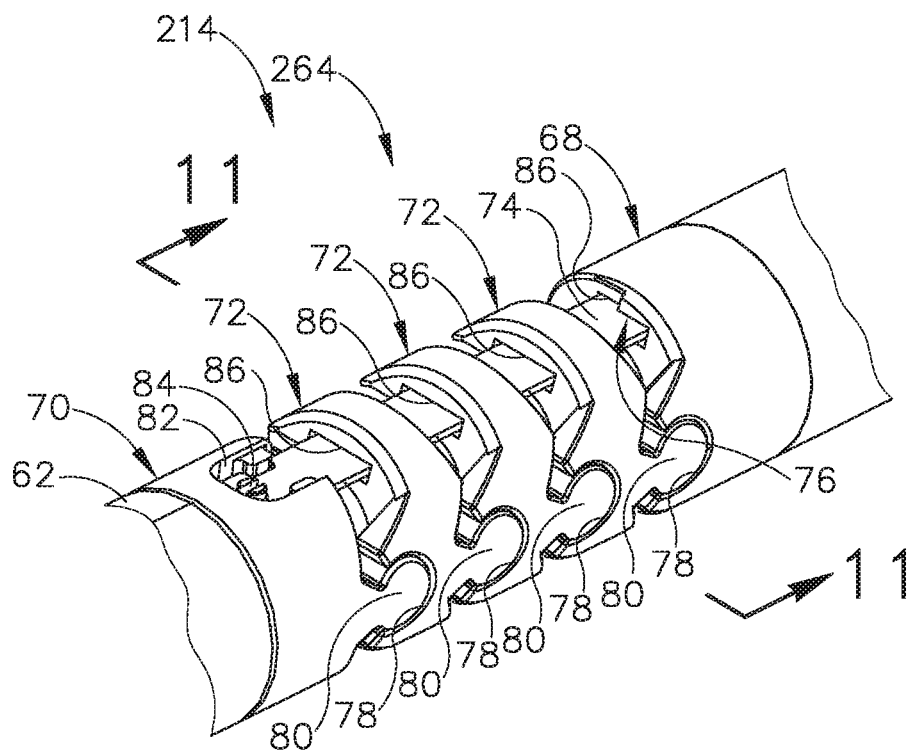
FIG. 10 depicts an enlarged, front perspective view of the distal articulation section of FIG. 8 in the straight configuration.
Figure 11:
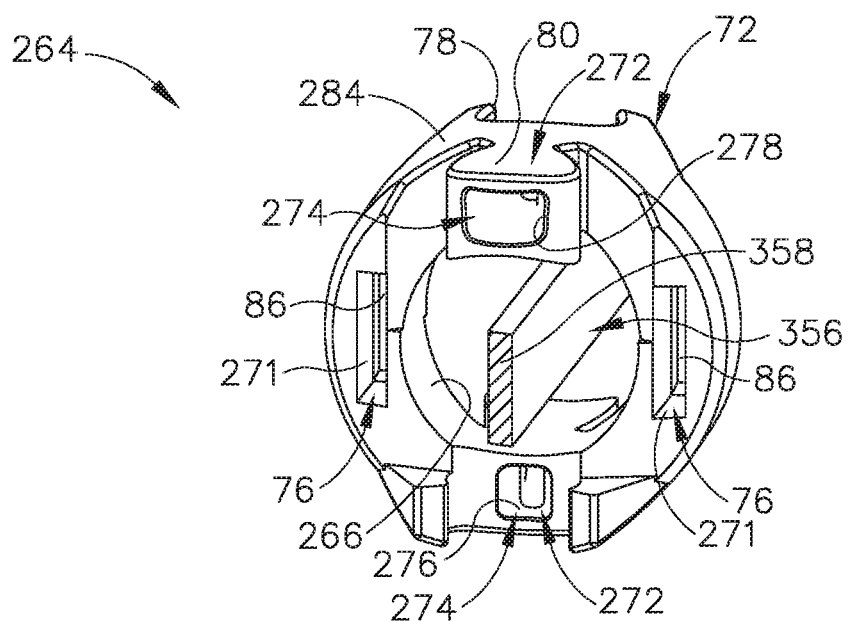
FIG. 11 depicts a sectional perspective view of the distal articulation section of FIG. 10 taken along section line 11-11 of FIG. 10 and having various components removed for additional clarity.
Figure 12:
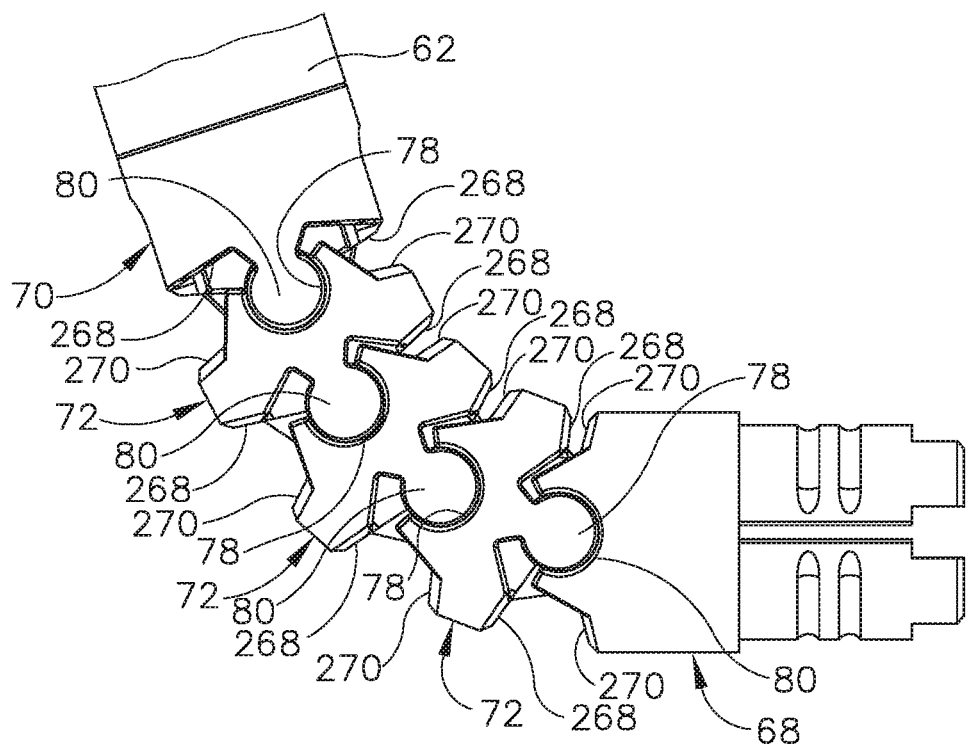
FIG. 12 depicts an enlarged, front view of the proximal articulation section of FIG. 8 in the proximal articulated configuration.
Figure 14:
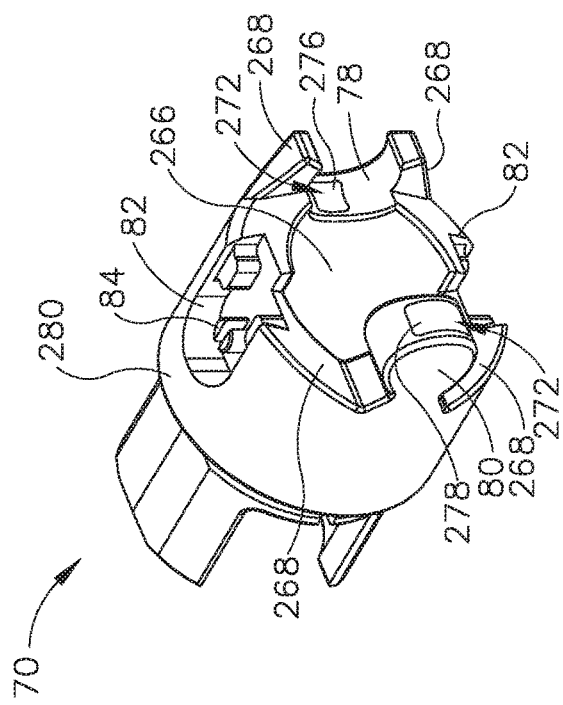
FIG. 14 depicts a rear, proximal perspective view of the distal link of FIG. 13.
Figure 13:
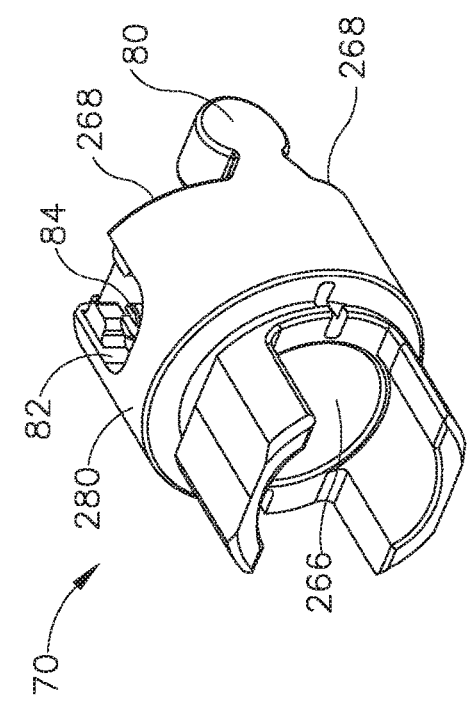
FIG. 13 depicts a rear, distal perspective view of a distal link of the proximal articulation section of FIG. 8.
Figure 16:
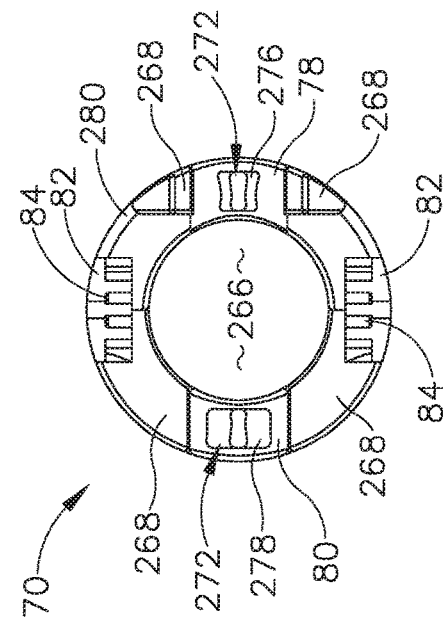
FIG. 16 depicts a proximal end elevational view of the distal link of FIG. 13.
Figure 15:
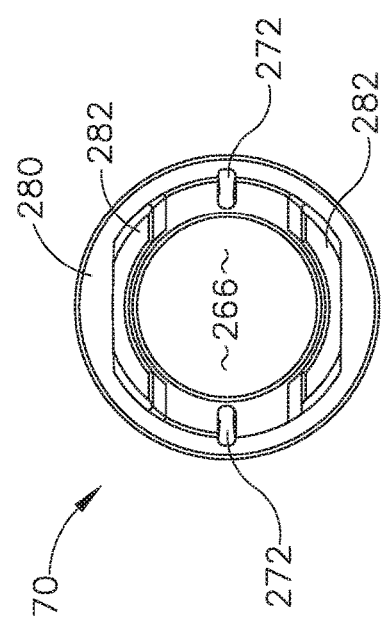
FIG. 15 depicts a distal end elevational view of the distal link of FIG. 13.
Figure 22:
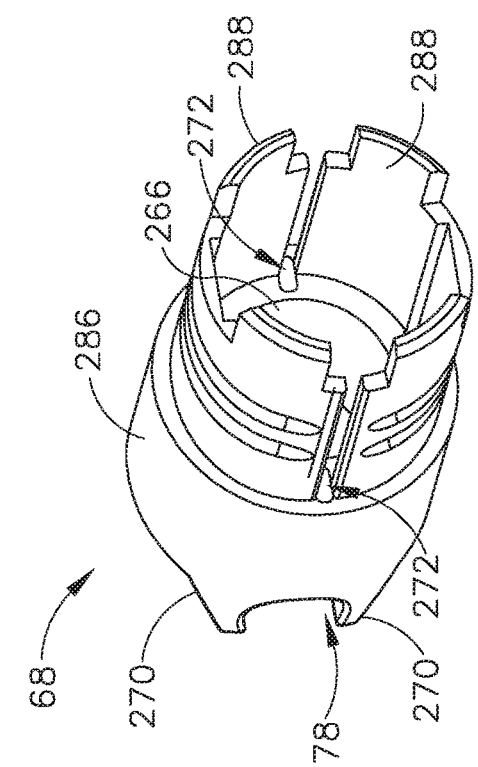
FIG. 22 depicts a rear, proximal perspective view of the proximal link of FIG. 21.
Figure 24:
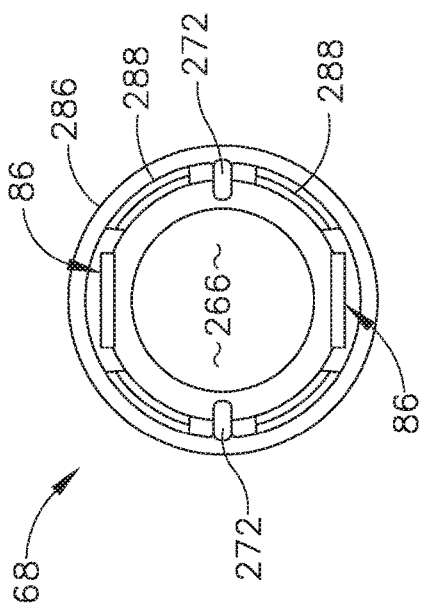
FIG. 24 depicts a proximal end elevational view of the proximal link of FIG. 21.
Figure 21:
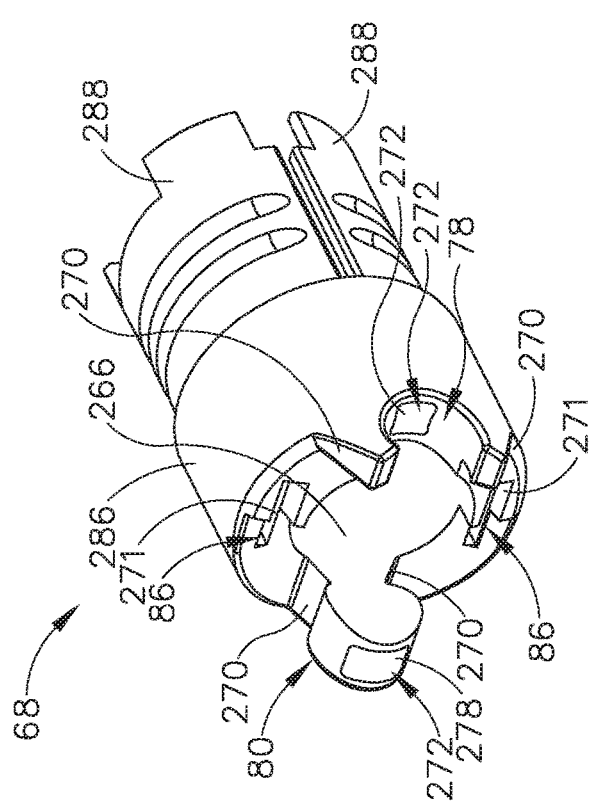
FIG. 21 depicts a rear, distal perspective view of a proximal link of the proximal articulation section of FIG. 8.
Figure 23:
FIG. 23 depicts a distal end elevational view of the proximal link of FIG. 21.

With respect to FIGS. 11-12, slots (86) in each link (68, 70, 72) that collectively define channels (76) are configured to slidably receive articulation bands (74) (see FIG. 10). Slots (86) also have drafted openings (271) to inhibit kinking of articulation bands (74) (see FIG. 10) during use. Additional control members (not shown), such as additional drivers (not shown), are also connected between end effector (16) (see FIG. 7) and base assembly (212) (see FIG. 7) and thus extend through distal articulation section (264) in the present example. These additional control members (not shown) are received through arcuate tongues and grooves (80, 78) along lateral centerline to inhibit changing lengths associated with articulation of distal articulation section (264). More particularly, a pair of passageways (272) longitudinally extend through each link (68, 70, 72) in alignment with arcuate tongues and grooves (80, 78) to collectively define a pair of additional channels (274) configured to guide control members (not shown) through distal articulation section (264). Each passageway (272) also has a widened groove opening (276) and a widened tongue opening (278) as respectively applicable to arcuate groove and tongues (78, 80) of links (68, 70, 72). Each of widened groove and tongue opening (276, 278) is drafted to inhibit kinking of additional control members (not shown) while articulating distal articulation section (264) as described herein. In one example, links (68, 70, 72) may further include a material sleeve (not shown) or material coating (not shown) configured to further inhibit kinking and/or inhibit damage to flexible portion (358) of acoustic waveguide (356) in case of incidental contact.

FIGS. 13-16 show distal link (70) in greater detail in one example having a distal link body (280) with proximally extending arcuate tongue (80) and proximally extending arcuate groove (78) with passageways (272). Distal link body (280) further includes distally extending coupling members (282) configured to be received within another portion of shaft assembly (214) (see FIG. 7) for rigidly connecting therewith. Notches (82) and pins (84) configured to connect to articulation bands (74) (see FIG. 10) are also shown angularly between arcuate tongue and groove (80, 78), whereas distal stops (268) are respectively positioned about arcuate tongue and groove (80, 78). Of course, distal link (70) may vary as desired for incorporating distal articulation section (264) (see FIG. 7) into shaft assembly (214) (see FIG. 7) such that the invention is not intended to be unnecessarily limited to the particular distal link (70) shown in the present example.

FIGS. 17-20 show intermediate link (72) in greater detail in one example having an intermediate link body (284) with proximally and distally extending arcuate tongues (80) and proximally and distally extending arcuate grooves (78) with passageways (272). Distal stops (268) are respectively positioned about distally facing arcuate tongue and groove (80, 78), whereas proximal stops (270) are respectively positioned about proximally facing arcuate tongue and groove (80, 78). Of course, intermediate link (72) may vary as desired for incorporating distal articulation section (264) (see FIG. 7) into shaft assembly (214) (see FIG. 7) such that the invention is not intended to be unnecessarily limited to the particular intermediate link (72) shown in the present example.

FIGS. 21-24 show proximal link (68) in greater detail in one example having a proximal link body (286) with distally extending arcuate tongue (80) and distally extending arcuate groove (78) with passageways (272). Proximal link body (286) further includes proximally extending coupling members (288) configured to be received within another portion of shaft assembly (214) (see FIG. 7) for rigidly connecting therewith. Slots (86) are configured to receive articulation bands (74) (see FIG. 10) and shown angularly between arcuate tongue and groove (80, 78), whereas proximal stops (270) are respectively positioned about arcuate tongue and groove (80, 78). Of course, proximal link (68) may vary as desired for incorporating distal articulation section (264) (see FIG. 7) into shaft assembly (214) (see FIG. 7) such that the invention is not intended to be unnecessarily limited to the particular proximal link (68) shown in the present example.

In use, referring back to FIGS. 7-8, the operator selectively directs proximal and distal articulation sections (64, 264) in order to deflect end effector (16) relative to longitudinal axis (61). In one example, proximal articulation section (64) articulates in order to deflect a distal remainder of shaft assembly (214) with end effector (16) through the pitch plane relative to axis (61) and then distal articulation section (264) articulates in order to deflect a further distal remainder of shaft assembly (214) with end effector (16) through the yaw plane relative to axis (374). In another example, distal articulation section (264) articulates in order to deflect the further distal remainder of shaft assembly (214) with end effector (16) through the yaw plane and then proximal articulation section (64) articulates in order to deflect a distal remainder of shaft assembly (214) with end effector (16) through the pitch plane. In still another example, proximal and distal articulation sections (64, 264) simultaneously articulate in order to deflect remainders of shaft assembly (14) and end effector through the pitch and yaw planes respectively. Alternatively, either one of proximal or distal articulation sections (64, 264) are articulated without articulating the remaining of the proximal or distal articulation sections (64, 264). In any case, end effector (16) is thereby configured to deflect through at least two distinct planes via one or more articulation sections (64, 264).

While the present example provides two distinct planes through which to move end effector (16) via two respective articulation sections (64, 264), an alternative articulation section may be configured to provide articulation in at least two distinct planes in a series of joints at discrete longitudinal positions, similar to shaft assembly (214) with articulation sections (64, 264), or in a single joint capable of articulating through at least two planes in one discrete longitudinal position. The invention is thus not intended to be unnecessarily limited to multiple articulation sections as shown in the present example for multi-planar articulation as will be appreciated in view of various multi-flex acoustic waveguides (356, 456, 556, 656, 756, 856) discussed below in greater detail.

B. Exemplary Acoustic Waveguides with Flexible Portions for Multi-Planar Articulation While movement of end effector (16) in six degrees of freedom may increase access to an anatomy of the patient during a surgical procedure for improved patient outcomes, such flexibility tends to strain components, particularly those components configured to communicate ultrasonic vibrations from transducer assembly (54) to ultrasonic blade (46). By way of example, acoustic waveguide (56) of ultrasonic surgical instrument (10) in FIG. 4A is configured to flex at one such flexible portion (58) within articulation section (64) through one plane, but further flexing through another plane would overly strain acoustic waveguide (56) resulting in damage and ultimately failure of acoustic waveguide (56). Such damage and failure of acoustic waveguide (56) tends to occur, because forced flexing of acoustic waveguide (56) generates stress concentrations in one or more locations along acoustic waveguide (56). In turn, these locations of stress concentrations within acoustic waveguide (56) continue to carry the ultrasonic vibrations, resulting in damage, fracture, and failure of acoustic waveguide (56) in use.

Multi-flex acoustic waveguides (356, 456, 556, 656, 756, 856) discussed below with respect to FIGS. 25-35B are thus configured to provide flexing in more than one plane with increased durability. More particularly, multi-flex acoustic waveguides (356, 456, 556, 656, 756, 856) have one or more structural formations configured to communicate ultrasonic vibrations while being flexed in one or more of a variety of available planes of deflection. While shaft assembly (214) (see FIG. 8) discussed above incorporates acoustic waveguide (356), it will be appreciated that any other waveguides (456, 556, 656, 756, 856) may also be incorporated into shaft assembly (214), such that the invention is not intended to be unnecessarily limited to use with shaft assembly (214) (see FIG. 8) discussed above. Like numbers below indicate like features described above in greater detail.

i. A First Exemplary Multi-Flex Acoustic Waveguide

Figure 25:
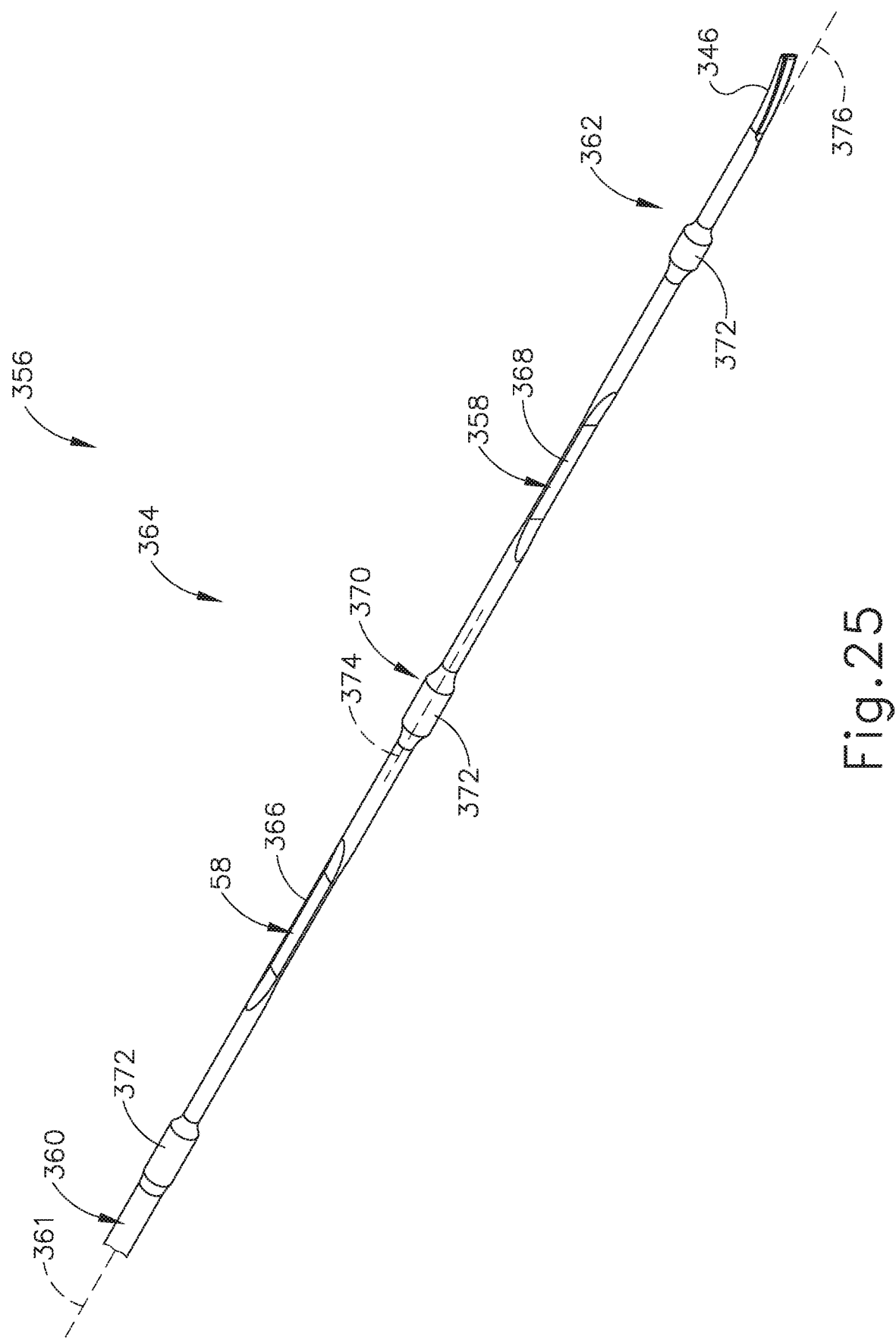
FIG. 25 a front perspective view of a first exemplary multi-flex acoustic waveguide having a flexible distal yaw ribbon and a flexible proximal pitch ribbon in a straight contour.

FIGS. 25-26 show the first exemplary multi-flex acoustic waveguide (356) having proximal flexible portion (58) and distal flexible portion (358) configured to respectively flex in a pitch direction through the pitch plane and in a yaw direction through the yaw plane. Acoustic waveguide (356) of the present example more particularly includes a proximal waveguide body portion (360) defining a longitudinal axis (361), a distal waveguide body portion (362) distally extending to an ultrasonic blade (346), and an articulation body portion (364) longitudinally extending therebetween. Articulation body portion (364) having proximal and distal flexible portions (58, 358) is thus configured to flex in the pitch and yaw directions to thereby deflect ultrasonic blade (346) relative to longitudinal axis (361) through the pitch and yaw planes for multi-planar deflection. In the present example of proximal waveguide body portion (360), articulation body portion (364), distal waveguide body portion (362), and ultrasonic blade (346) have a single, unitary construction, although multi-flex acoustic waveguide (356) may be alternatively constructed with one or more connected structures. The invention is thus not intended to be unnecessarily limited to single, unitary construction of multi-flex acoustic waveguide (356) shown in the present example.

More particularly, proximal flexible portion (58) includes a flexible proximal pitch ribbon (366), whereas distal flexible portion (358) includes a flexible distal yaw ribbon (368). Articulation body portion (364) also includes an intermediate waveguide body portion (370), extending between and in direct connection with flexible proximal pitch ribbon (366) and flexible distal yaw ribbon (368). Bosses (372) are positioned on waveguide body portions (360, 362, 370) and respectively spaced apart from each other so as to coincide with and, more particularly, be centered on respective acoustic nodes along multi-flex acoustic waveguide (356). Similarly, flexible proximal pitch ribbon (366) is positioned and centered on an acoustic antinode of multi-flex acoustic waveguide (356), while flexible distal yaw ribbon (368) is also positioned and centered on another acoustic antinode of multi-flex acoustic waveguide (356).

FIGS. 25-26 show multi-flex acoustic waveguide (356) with each of flexible proximal pitch ribbon (366) and flexible distal yaw ribbon (368) in a linear form such that multi-flex acoustic waveguide (356) has a straight contour. Each ribbon (366, 368) is thereby configured to communicate ultrasonic vibrations in the straight contour longitudinally toward ultrasonic blade (346) during use. Selectively bending flexible proximal pitch ribbon (366) relative to longitudinal axis (361) away from longitudinal axis (361) results in one of any available arcuate contours for flexible proximal pitch ribbon (366). Alternatively or in addition, selectively bending flexible distal yaw ribbon (368) relative an intermediate axis (374) defined by intermediate waveguide body portion (370) away from intermediate axis (374) results in one of any available arcuate contours for flexible distal yaw ribbon (368). In one example, articulation body portion (364) extends along the arcuate contour of only one of flexible proximal pitch ribbon (366) or flexible distal yaw ribbon (368) such that ultrasonic blade (346) deflects through one of two available planes along a blade axis (376). In another example, articulation body portion (364) extends along the arcuate contour of both flexible proximal pitch ribbon (366) and flexible distal yaw ribbon (368) for a dual arcuate contour such that ultrasonic blade (346) deflects through each of two available planes along blade axis (376). While the present example has ribbons (366, 368) angularly oriented perpendicular to each to each other, one or both ribbons (366, 368) may have any relative angular orientation and are not intended to be limited to the angular orientation as shown and described herein.

ii. A Second Exemplary Multi-Flex Acoustic Waveguide

FIG. 27 shows a second exemplary multi-flex acoustic waveguide (456) having a proximal flexible portion (458a) and a distal flexible portion (458b) configured to respectively flex in a yaw direction through a proximal yaw plane and again in a yaw direction through a distal yaw plane. Acoustic waveguide (456) of the present example more particularly includes a proximal waveguide body portion (460) defining a longitudinal axis (461), a distal waveguide body portion (462) distally extending to an ultrasonic blade (446), and an articulation body portion (464) longitudinally extending therebetween. Articulation body portion (464) having proximal and distal flexible portions (458a, 458b) is thus configured to flex in the yaw direction at multiple locations to thereby deflect ultrasonic blade (446) relative to longitudinal axis (461) through multiple yaw planes for multi-planar deflection. In the present example proximal waveguide body portion (460), articulation body portion (464), distal waveguide body portion (462), and ultrasonic blade (446) have a single, unitary construction, although multi-flex acoustic waveguide (456) may be alternatively constructed with one or more connected structures. The invention is thus not intended to be unnecessarily limited to single, unitary construction of multi-flex acoustic waveguide (456) shown in the present example.

More particularly, proximal flexible portion (458a) includes a flexible proximal yaw ribbon (466), whereas distal flexible portion (458b) includes a flexible distal yaw ribbon (468). Articulation body portion (464) also includes an intermediate waveguide body portion (470), extending between and in direct connection with flexible proximal yaw ribbon (466) and flexible distal yaw ribbon (468). Bosses (not shown) may be positioned on waveguide body portions (360, 362, 370) and respectively spaced apart from each other so as to coincide with and, more particularly, be centered on respective acoustic nodes along multi-flex acoustic waveguide (456). Similarly, flexible proximal yaw ribbon (466) is positioned and centered on an acoustic antinode of multi-flex acoustic waveguide (456), while flexible distal yaw ribbon (468) is also positioned and centered on another acoustic antinode of multi-flex acoustic waveguide (456).

Each ribbon (436, 468) is configured to communicate ultrasonic vibrations in a straight contour longitudinally toward ultrasonic blade (446) during use. Selectively bending flexible proximal yaw ribbon (466) relative to longitudinal axis (461) away from longitudinal axis (461) results in one of any available arcuate contours for flexible proximal yaw ribbon (466). Alternatively or in addition, selectively bending flexible distal yaw ribbon (468) relative an intermediate axis (474) defined by intermediate waveguide body portion (470) away from intermediate axis (474) results in one of any available arcuate contours for flexible distal yaw ribbon (468). In one example, articulation body portion (464) extends along the arcuate contour of only one of flexible proximal yaw ribbon (466) or flexible distal yaw ribbon (468) such that ultrasonic blade (446) deflects through one of two available planes along a blade axis (476). In another example, articulation body portion (464) extends along the arcuate contour of both flexible proximal yaw ribbon (466) and flexible distal yaw ribbon (468) for a dual arcuate contour such that ultrasonic blade (446) deflects through each of two available planes along blade axis (476) and as shown in FIG. 27. While the present example has ribbons (466, 468) in the same angular orientation, one or both ribbons (466, 468) may have any relative angular orientation and are not intended to be limited to the angular orientation as shown and described herein.

iii. A Third Exemplary Multi-Flex Acoustic Waveguide

FIGS. 28-30B show a third exemplary multi-flex acoustic waveguide (556) having a flexible portion (558) configured to flex in a full 360-degree range of radial directions through a respective full 360-degree range of radial planes. Acoustic waveguide (556) of the present example more particularly includes a proximal waveguide body portion (560) defining a longitudinal axis (561), a distal waveguide body portion (562) distally extending to an ultrasonic blade (546), and an articulation body portion (564) longitudinally extending therebetween. Articulation body portion (564) having flexible portion (558) is thus configured to flex in any radial direction about longitudinal axis (561) to thereby deflect ultrasonic blade (546) relative to longitudinal axis (561) through any respective radial plane for multi-planar deflection. In the present example, proximal waveguide body portion (560), articulation body portion (564), distal waveguide body portion (562), and ultrasonic blade (546) have a single, unitary construction, although multi-flex acoustic waveguide (556) may be alternatively constructed with one or more connected structures. The invention is thus not intended to be unnecessarily limited to single, unitary construction of multi-flex acoustic waveguide (556) shown in the present example.

Figure 28:
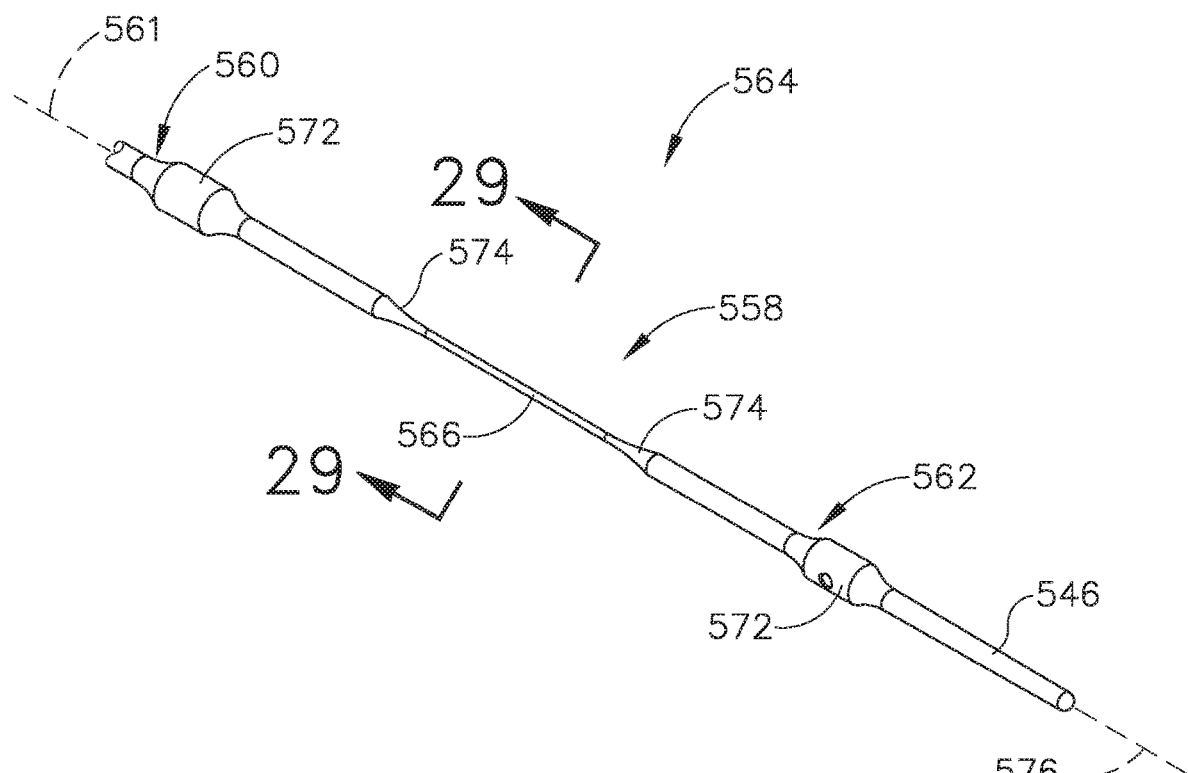
FIG. 28 depicts a front perspective view of a third exemplary multi-flex acoustic waveguide having a first example of a flexible wire in a straight contour.
Figure 29:
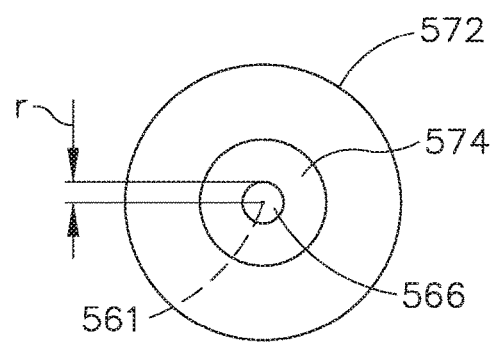
FIG. 29 depicts a cross-sectional view of the acoustic waveguide of FIG. 28 taken along section line 29-29 of FIG. 28.

More particularly, as shown in FIGS. 28-29, flexible portion (558) includes a first example of a flexible wire (566) configured to flex in any radial direction about longitudinal axis (561) to thereby deflect ultrasonic blade (546) relative to longitudinal axis (561) through any respective radial plane for multi-planar deflection. Flexible wire (566) is elongated and cylindrical defining a wire cross-sectional radius (r). Bosses (572) are positioned on waveguide body portions (560, 562) and are respectively spaced apart from each other so as to coincide with and, more particularly, be centered on respective acoustic nodes along multi-flex acoustic waveguide (556). Similarly, flexible wire (566) is positioned and centered on an acoustic antinode of multi-flex acoustic waveguide (556). Each proximal and distal waveguide body portion (560, 562) is more rigid than flexible wire (566) and has a conical taper (574) narrowing toward flexible wire (566). Between conical tapers (574) and bosses (572), proximal and distal waveguide body portions (560, 562) each define a waveguide body radius. In the present example, waveguide body radius is larger than wire cross-sectional radius (r).

Figure 30A:
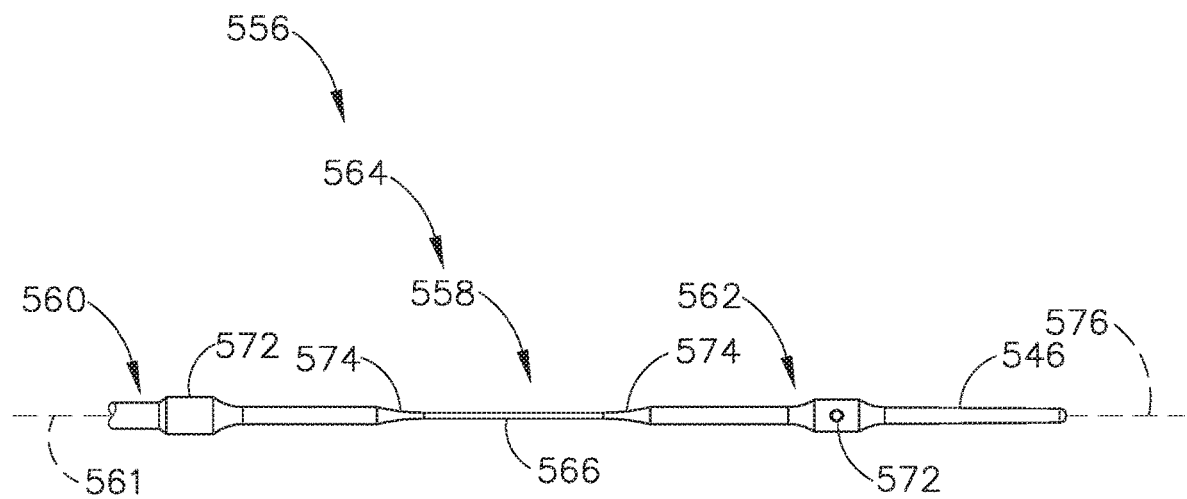
FIG. 30A depicts a top view of the acoustic waveguide of FIG. 28 with the flexible wire in the straight contour.
Figure 30B:
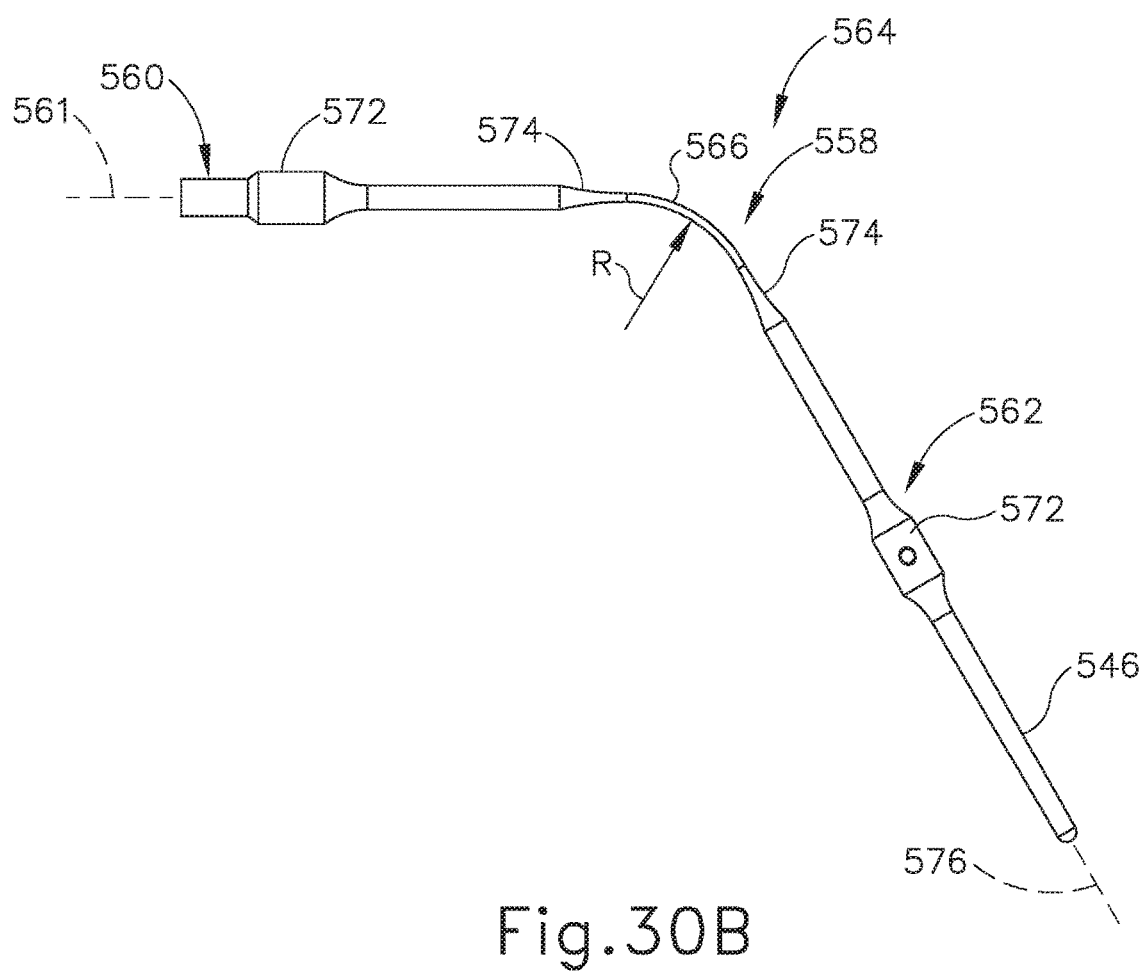
FIG. 30B depicts the top view of the acoustic waveguide similar to FIG. 30A, but with the flexible wire in an exemplary arcuate contour.

FIG. 30A shows multi-flex acoustic waveguide (556) with flexible wire (566) in a linear form such that multi-flex acoustic waveguide (556) has a straight contour. Flexible wire (566) is thereby configured to communicate ultrasonic vibrations in the straight contour longitudinally toward ultrasonic blade (546) during use. Selectively bending flexible wire (566) relative to longitudinal axis (561) away from longitudinal axis (561) results in one of any available arcuate contours for flexible wire (566) with ultrasonic blade (346) deflecting through one of any available radial plane along a blade axis (376) and about a bend radius (R). One example of such bend radius (R) is shown in FIG. 30B. With the arcuate contour, flexible wire (566) is configured to uncouple a longitudinal vibrational component of the ultrasonic vibration from a transverse vibrational component of the ultrasonic vibration to thereby communicate the ultrasonic vibration about the bent flexible wire (566) without damaging flexible wire (566) or substantially degrading the ultrasonic vibration during use.

To this end, acoustic waveguide (556) has a set of predetermined properties to uncouple the longitudinal vibrational component of the ultrasonic vibration from the transverse vibrational component of the ultrasonic vibration during use. In the present example, the predetermined properties include wire cross-sectional radius (r) and bend radius (R) discussed above in addition to a plurality of wire material properties, including an elastic modulus (E) of flexible wire (566), a yield strength ($\sigma_y$) of flexible wire (566), a natural frequency (f) of flexible wire (566), as well as a constant, the speed of sound (c). Given that bend radius (R) may vary, predetermined properties further include a first condition, a second condition, and a third condition that accommodate a range of available bend radii (R) while still effectively uncoupling the longitudinal vibrational component of the ultrasonic vibration from the transverse vibrational component of the ultrasonic vibration during use. As shown in one example, these conditions are as follows.

First Condition: $\dfrac{r}{R} < 0.1$

Second Condition: $R > \dfrac{c}{2\pi f}$

Third Condition: $\dfrac{8Er}{\pi^2 R} < \sigma_y$

While the particular material, sizing, and bend of flexible wire (566) may vary to achieve uncoupling of the longitudinal vibrational component of the ultrasonic vibration from the transverse vibrational component of the ultrasonic vibration, in one example the material is a nitinol material. In another example, the material of flexible wire (566) is a titanium material. The invention is thus not intended to be unnecessarily limited to the particular material, sizing, and bend of flexible wire (566) as shown and described herein.

With respect to FIG. 30B, flexible wire (566) has one bend about an acoustic antinode with bend radius (R). Alternatively or in addition, an alternative flexible wire (not shown) may have an additional bend (not shown) about another antinode such that flexible wire (not shown) is configured to bend at two or more positions during use, similar to dual flexible portions (58, 358, 458a, 458b) (see FIGS. 25-27) associated with acoustic waveguides (356, 456) (see FIGS. 25-27) discussed above in greater detail. Such an alternative flexible wire (not shown) may be offset from flexible wire (566) with an intermediate waveguide body portion (not shown) therebetween similar to acoustic waveguides (356, 456) (see FIGS. 25-27) or without intermediate waveguide body portion (not shown) such that alternative flexible wire (not shown) and flexible wire (566) are essentially continuous therealong. The invention is thus not intended to be unnecessarily limited to the arrangement of one flexible wire (566) as shown in the present example.

iv. A Fourth Exemplary Multi-Flex Acoustic Waveguide

Figure 31:
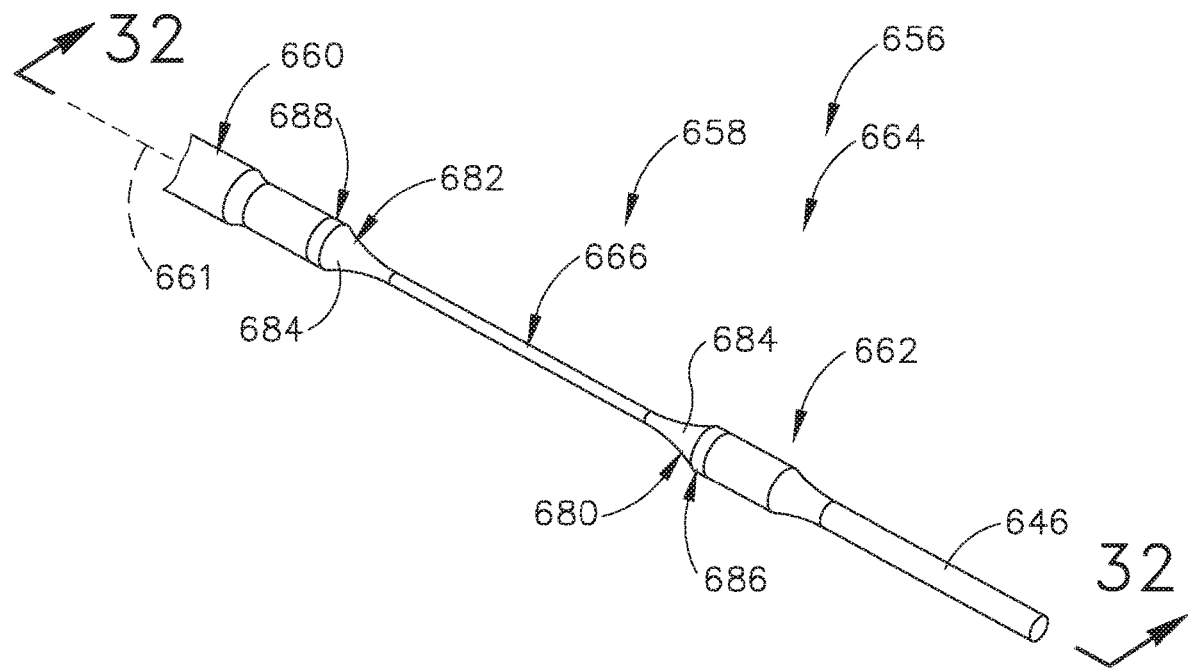
FIG. 31 depicts a front perspective view of a fourth exemplary multi-flex acoustic waveguide having a second example of a flexible wire in a straight contour
Figure 32:
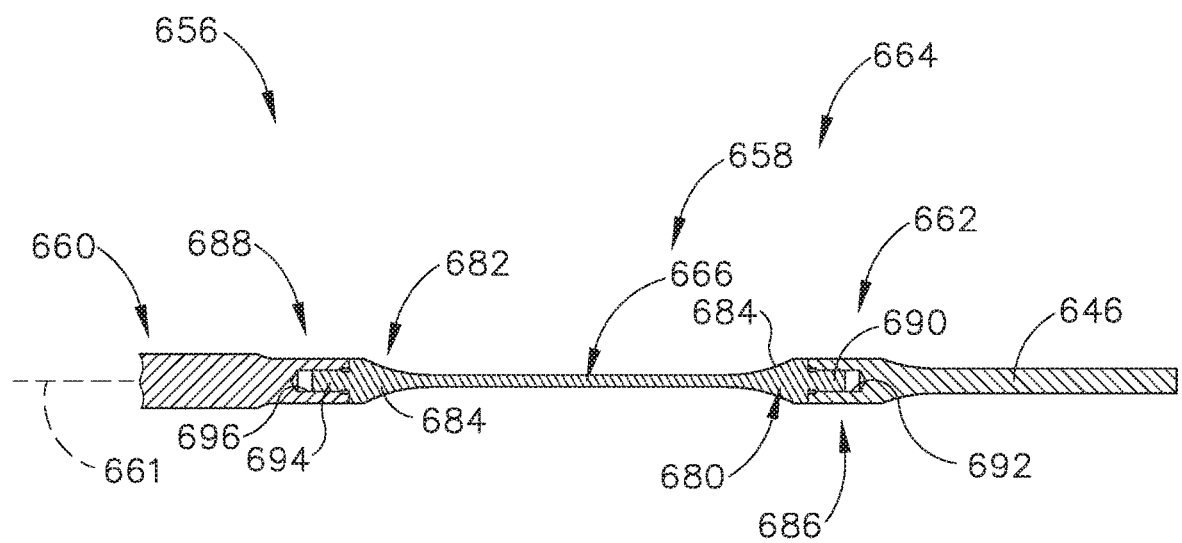
FIG. 32 depicts a cross-sectional view of the acoustic waveguide of FIG. 31 taken along section line 32-32 of FIG. 31.

FIGS. 31-32 show a fourth exemplary multi-flex acoustic waveguide (656) having a flexible portion (658) configured to flex in a full 360-degree range of radial directions through a respective full 360-degree range of radial planes. Acoustic waveguide (656) of the present example more particularly includes a proximal waveguide body portion (660) defining a longitudinal axis (661), a distal waveguide body portion (662) distally extending to an ultrasonic blade (646), and an articulation body portion (664) longitudinally extending therebetween. Articulation body portion (664) having flexible portion (658) is thus configured to flex in any radial direction about longitudinal axis (661) to thereby deflect ultrasonic blade (646) relative to longitudinal axis (661) through any respective radial plane for multi-planar deflection.

More particularly, flexible portion (658) includes a second example of a flexible wire (666) configured to flex in any radial direction about longitudinal axis (661) to thereby deflect ultrasonic blade (646) relative to longitudinal axis (661) through any respective radial plane for multi-planar deflection. In this respect, acoustic waveguide (656) is similar to acoustic waveguide (556) (see FIG. 28), but, rather than being unitarily constructed, acoustic waveguide (656) is assembled via several discrete components. Flexible wire (666) is like flexible wire (566) (see FIG. 28) discussed above in other respects unless otherwise stated below.

As shown in the present example, flexible portion (658) further includes a distal wire end portion (680) opposite from a proximal wire end portion (682) with flexible wire (666) extending therebetween. Distal and proximal wire end portions (680, 682) each have a conical taper (684) narrowing toward flexible wire (666). Extending opposite from respective conical tapers (684), distal end proximal wire end portions (680, 682) further respectively include a distal coupling (686) configured to connect to distal waveguide body portion (662) and a proximal coupling (688) configured to connect to proximal waveguide body portion (660). As shown in the present example, distal coupling (686) includes a distal threaded stud (690) distally extending from distal wire end portion (680) and a distal threaded bore (692) in distal waveguide body portion (662). Distal threaded stud (690) mechanically and acoustically couples into distal threaded bore (692) to connect flexible wire (666) to distal waveguide body portion (662). Similarly, proximal coupling (688) includes a proximal threaded stud (694) proximally extending from proximal wire end portion (682) and a proximal threaded bore (696) in proximal waveguide body portion (660). Proximal threaded stud (694) mechanically and acoustically couples into proximal threaded bore (696) to connect flexible wire (666) to proximal waveguide body portion (660).

With acoustic waveguide (656) assembled via several discrete components, one or more of proximal waveguide body portion (660), distal waveguide body portion (662), and articulation body portion (664) may be formed from differing materials. By way of example, proximal waveguide body portion (660) is formed from one of titanium material, aluminum, material, or nitinol material. In addition, distal waveguide body portion (662), which includes ultrasonic blade (646), is formed from one of titanium material or nitinol material. Similarly, articulation body portion (664) is formed from one of titanium material or nitinol material. Any combination of such materials may be incorporated into acoustic waveguide (656) and thus configured to uncouple the longitudinal vibrational component of the ultrasonic vibration from the transverse vibrational component of the ultrasonic vibration based on the set of predetermined properties discussed above in greater detail. While the present example incorporates threads into acoustic waveguide (656) for connecting various components of differing materials, such connections may additionally or alternatively include swaging, welding, temperature fits, and/or shape memory fits. The invention is thus not intended to be unnecessarily limited to the particular threaded couplings (686, 688) shown and described in the present example.

v. A Fifth Exemplary Multi-Flex Acoustic Waveguide

Figure 33:
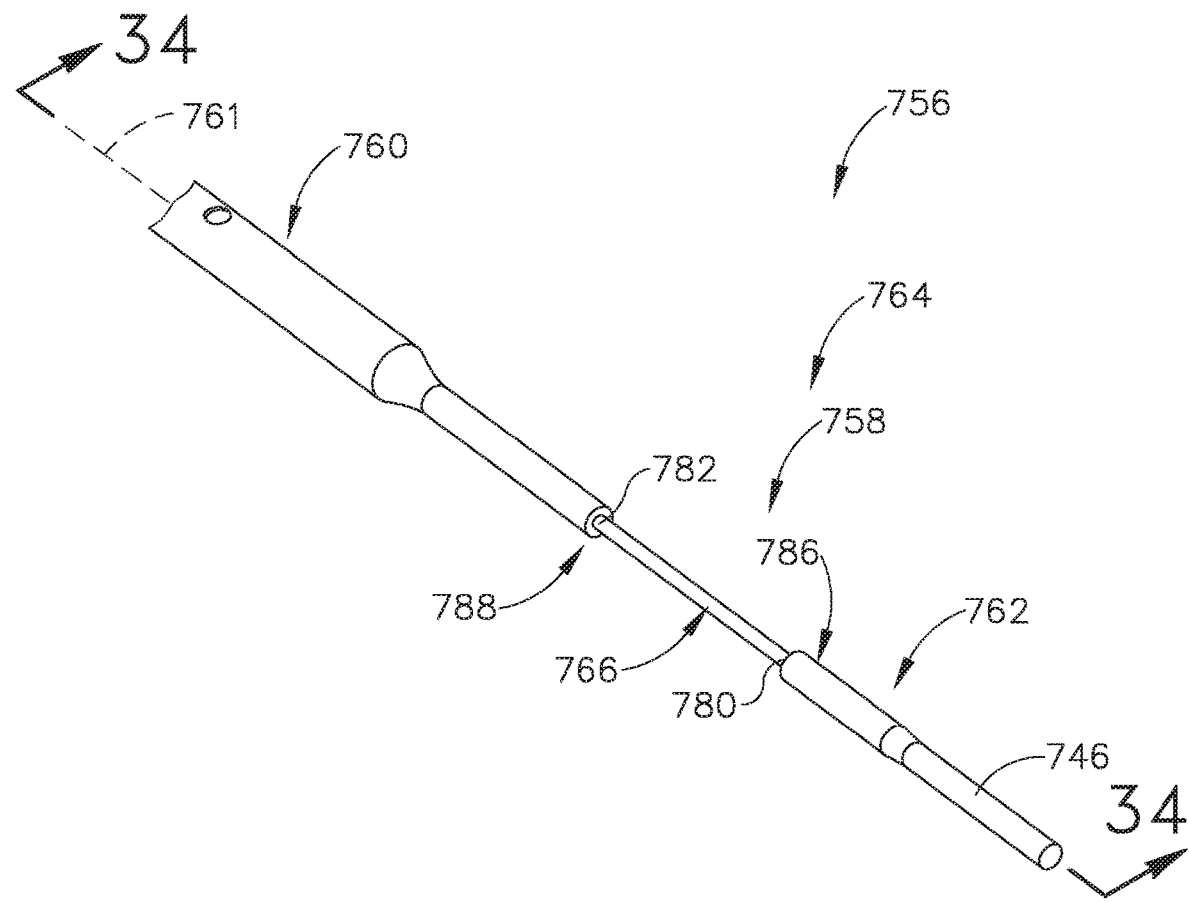
FIG. 33 depicts a front perspective view of a fifth exemplary multi-flex acoustic waveguide having a third example of a flexible wire in a straight contour.
Figure 34:
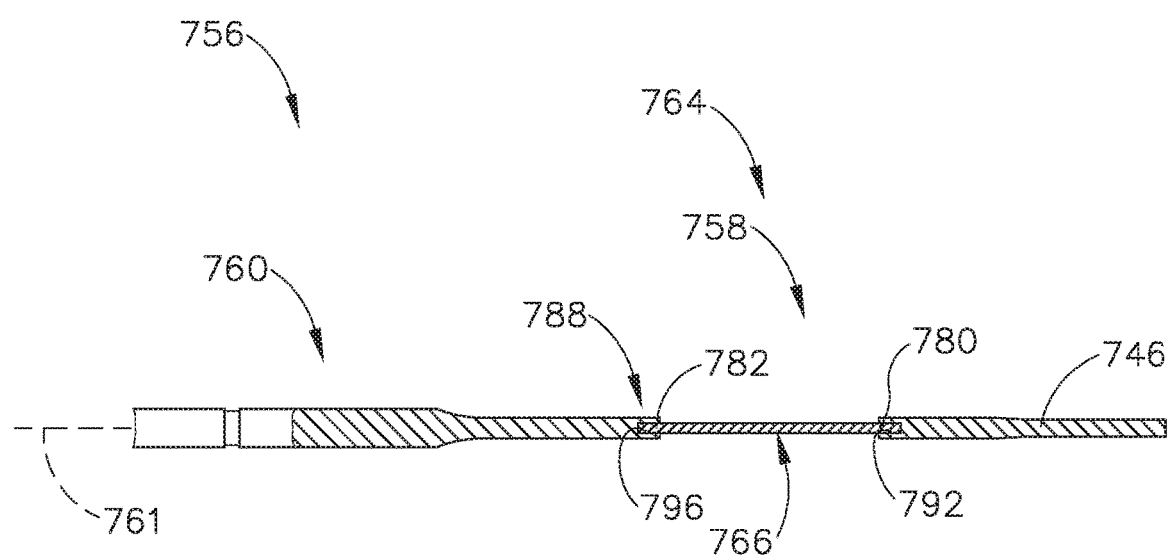
FIG. 34 depicts a cross-sectional view of the acoustic waveguide of FIG. 33 taken along section line 34-34 of FIG. 33.

FIGS. 33-34 show a fifth exemplary multi-flex acoustic waveguide (756) having a flexible portion (758) configured to flex in a full 360-degree range of radial directions through a respective full 360 degree range of radial planes. Acoustic waveguide (756) of the present example more particularly includes a proximal waveguide body portion (760) defining a longitudinal axis (761), a distal waveguide body portion (762) distally extending to an ultrasonic blade (746), and an articulation body portion (764) longitudinally extending therebetween. Articulation body portion (764) having flexible portion (758) is thus configured to flex in any radial direction about longitudinal axis (761) to thereby deflect ultrasonic blade (746) relative to longitudinal axis (761) through any respective radial plane for multi-planar deflection.

More particularly, flexible portion (758) includes a third example of a flexible wire (766) configured to flex in any radial direction about longitudinal axis (761) to thereby deflect ultrasonic blade (746) relative to longitudinal axis (761) through any respective radial plane for multi-planar deflection. In this respect, acoustic waveguide (756) is similar to acoustic waveguide (556) (see FIG. 28), but, rather than being unitarily constructed, acoustic waveguide (756) is assembled via several discrete components. Flexible wire (766) is like flexible wire (566) (see FIG. 28) discussed above in other respects unless otherwise stated below.

As shown in the present example, flexible portion (758) further includes a distal wire end portion (780) opposite from a proximal wire end portion (782) with flexible wire (766) extending therebetween. Distal and proximal wire end portions (780, 782) respectively include a distal coupling (786) configured to connect to distal waveguide body portion (762) and a proximal coupling (788) configured to connect to proximal waveguide body portion (760). As shown in the present example, distal coupling (786) includes distal wire end portion (780) and a distal bore (792) in distal waveguide body portion (762). Distal wire end portion (780) is swaged into distal bore (792) to thereby mechanically and acoustically couple flexible wire (766) to distal waveguide body portion (762). Similarly, proximal coupling (788) includes proximal wire end portion (682) and a proximal bore (796) in proximal waveguide body portion (760). Proximal wire end portion (782) is swaged into proximal bore (796) to thereby mechanically and acoustically couple flexible wire (766) to proximal waveguide body portion (760).

With acoustic waveguide (756) assembled via several discrete components, one or more of proximal waveguide body portion (760), distal waveguide body portion (762), and articulation body portion (764) may be formed from differing materials. By way of example, proximal waveguide body portion (760) is formed from one of titanium material, aluminum, material, or nitinol material. In addition, distal waveguide body portion (762), which includes ultrasonic blade (746), is formed from one of titanium material or nitinol material. Similarly, articulation body portion (764) is formed from one of titanium material or nitinol material. Any combination of such materials may be incorporated into acoustic waveguide (756) and thus configured to uncouple the longitudinal vibrational component of the ultrasonic vibration from the transverse vibrational component of the ultrasonic vibration based on the set of predetermined properties discussed above in greater detail. While the present example swages portions of acoustic waveguide (656) together for connecting various components of differing materials, such connections may additionally or alternatively include threading, welding, temperature fits, and/or shape memory fits. The invention is thus not intended to be unnecessarily limited to the particular swaging shown and described in the present example.

vi. A Sixth Exemplary Multi-Flex Acoustic Waveguide

Figure 35A:
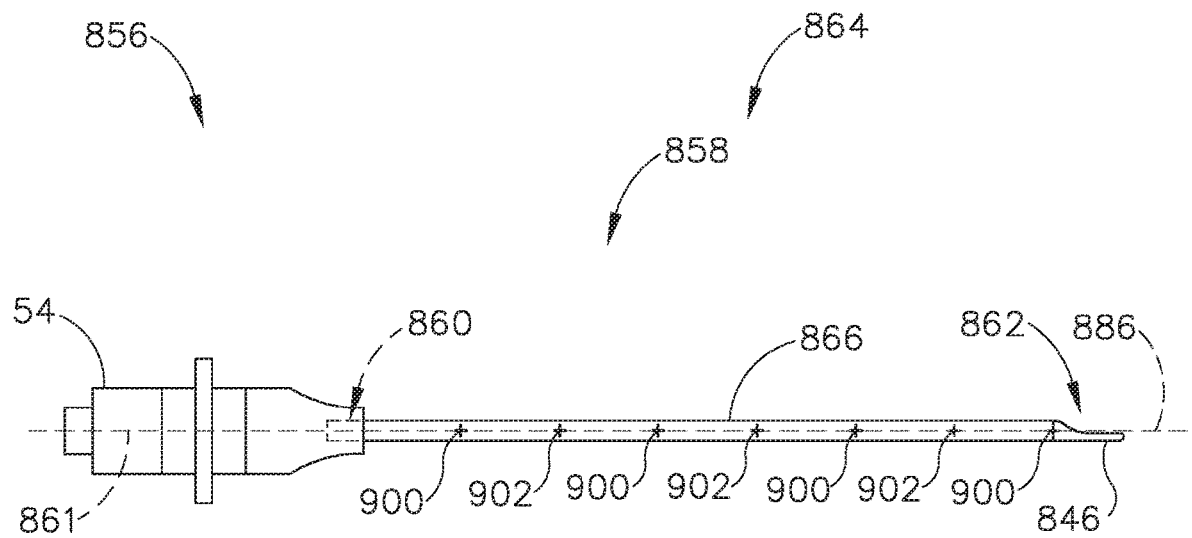
FIG. 35A depicts a top view of a sixth exemplary multi-flex acoustic waveguide with a flexible waveguide body in the straight contour.
Figure 35B:
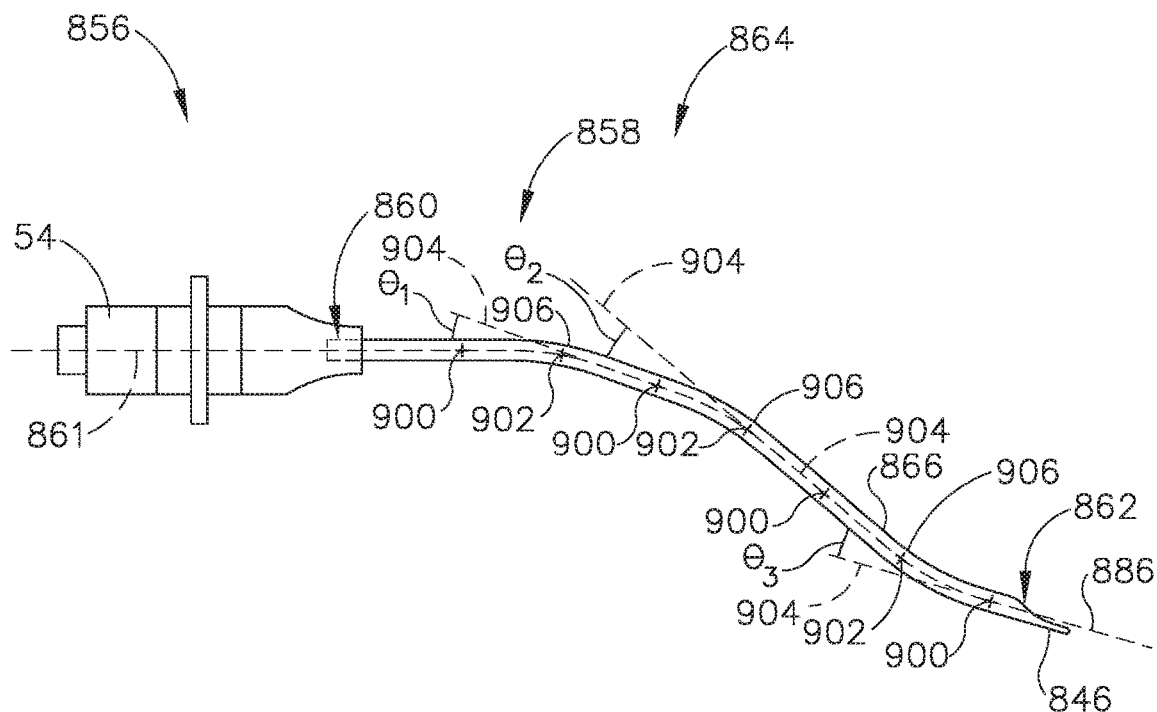
FIG. 35B depicts the top view of the acoustic waveguide similar to FIG. 35A, but with the flexible waveguide body in an exemplary arcuate contour.

FIGS. 35A-35B show a sixth exemplary multi-flex acoustic waveguide (856) having a flexible portion (858) configured to flex in a full 360-degree range of radial directions through a respective full 360-degree range of radial planes. Acoustic waveguide (856) of the present example more particularly includes a proximal waveguide body portion (860) defining a longitudinal axis (861), a distal waveguide body portion (862) distally extending to an ultrasonic blade (846), and an articulation body portion (864) longitudinally extending therebetween. Articulation body portion (864) having flexible portion (858) is thus configured to flex in any radial direction about longitudinal axis (861) to thereby deflect ultrasonic blade (846) relative to longitudinal axis (861) through any respective radial plane for multi-planar deflection. In the present example, proximal waveguide body portion (860), articulation body portion (864), distal waveguide body portion (862), and ultrasonic blade (846) have a single, unitary construction, although multi-flex acoustic waveguide (856) may be alternatively constructed with one or more connected structures. The invention is thus not intended to be unnecessarily limited to single, unitary construction of multi-flex acoustic waveguide (856) shown in the present example.

More particularly, flexible portion (558) includes an elongate flexible wire (866) extending essentially an entire length of articulation body portion (864) such that proximal waveguide body portion (860) is a proximal portion of acoustic waveguide (856) configured to be received within transducer assembly (54) and distal waveguide body portion (862) is generally ultrasonic blade (846). A majority of acoustic waveguide (856) is thus elongate flexible wire (866), which extends along a plurality of acoustic nodes (900) and a plurality of acoustic antinodes (902). Thus, elongate flexible wire (866) is configured to flex in any radial direction about longitudinal axis (861) as well as further flex in any radial direction about axes (904), which are positioned and aligned at acoustic nodes (902), respectively. Furthermore, elongate flexible wire (858) of the present example includes a plurality of flexible wire portions (906) respectively centered at acoustic antinodes (902) of multi-flex acoustic waveguide (856). Flexible wire portions (906) and intermediate wire portions are thus continuous to define elongate flexible wire (866) in the present example.

FIG. 35A shows multi-flex acoustic waveguide (856) with elongate flexible wire (866) in a linear form such that multi-flex acoustic waveguide (856) has a straight contour. Flexible wire (866) is thereby configured to communicate ultrasonic vibrations in the straight contour longitudinally toward ultrasonic blade (846) during use. Selectively bending flexible wire (866) at any flexible wire portion (906) relative to axes (861, 904) results in one of any available arcuate contours for elongate flexible wire (866) with ultrasonic blade (846) deflecting through one of any available radial planes along a blade axis (876). With the arcuate contour shown in FIG. 35B, elongate flexible wire (866) is configured to uncouple a longitudinal vibrational component of the ultrasonic vibration from a transverse vibrational component of the ultrasonic vibration to thereby communicate the ultrasonic vibration about the bent flexible wire (866) without damaging flexible wire (866) or substantially degrading the ultrasonic vibration during use. Such vibrational uncoupling is based on the set of predetermined properties discussed above in greater detail.

While the particular material, sizing, and bend of flexible wire (866) may vary to achieve uncoupling of the longitudinal vibrational component of the ultrasonic vibration from the transverse vibrational component of the ultrasonic vibration, in one example the material is a nitinol material. In another example, the material of flexible wire (866) is a titanium material. In any case, the invention is thus not intended to be unnecessarily limited to the particular material, sizing, and bend of flexible wire (866) as shown and described herein.

III. Ultrasonic Blades with Backcutting Edge and Circumferential Sealing

With respect to FIGS. 3A-3B discussed above in greater detail, clamp arm (44) is configured to rotate about blade (46) and also relative to shaft assembly (14) as indicated by arrow (53). In one example, clamp arm (44) selectively rotates in the clockwise or counterclockwise directions around blade (46) such that the operator selectively fixes clamp arm (44) angularly about blade (46) to thereby clamp tissue between blade (46) and clamp arm (44) with increased access to the tissue. While clamping between blade (46) and clamp arm (44), the operator selectively activates blade (46) with ultrasonic vibrations and, in one example, seals the tissue clamped therebetween. As shown in the present example, blade (46) has a blade body (910) longitudinally extending to a hemispherical distal end tip (912). Blade body (910) and hemispherical distal end tip (912) are generally rounded smooth and free of edges such that blade (46) is axisymmetric and has a full, circular circumferential sealing profile angularly about an entirety of longitudinal axis (61). This full, circular circumferential sealing profile represents engagement between rounded smooth surfaces of blade (46) and clamp pad (48) such that tissue sealing may occur around an entirety of blade (46) with clamp pad (48) clamping tissue thereagainst.

In some instances, it may be desirable to incorporate backcutting functionality into blade (46) while retaining a majority of the circumferential sealing profile about blade (46) for sealing tissue against clamp pad (48). Various examples of ultrasonic blades (1046, 1146) with backcutting edges (1048, 1148) for providing such backcutting functionality to the operator are described below in greater detail with respect to FIGS. 36-39. While backcutting edges (1048, 1148) may be incorporated into blade (46) (see FIG. 3A), the invention is not intended to be unnecessarily limited to including backcutting functionality. Moreover, it will be appreciated that alternative backcutting edges (not shown) may also have a circumferential sealing profile about a majority of a circumferential blade profile such that the invention is also not intended to be limited to the particular backcutting edges (1048, 1148) shown and described herein.

A. First Exemplary Backcutting Edge

Figure 36:
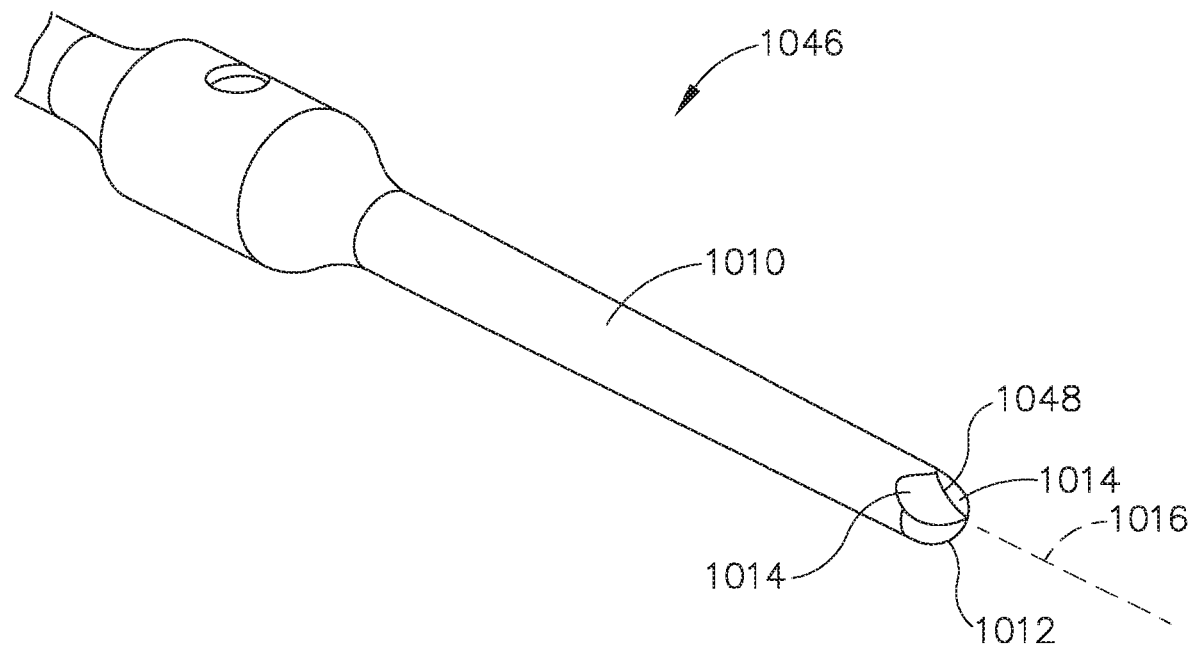
FIG. 36 depicts a perspective view of an ultrasonic blade with a first example of a circumferential blade profile having a first backcutting edge.
Figure 37:
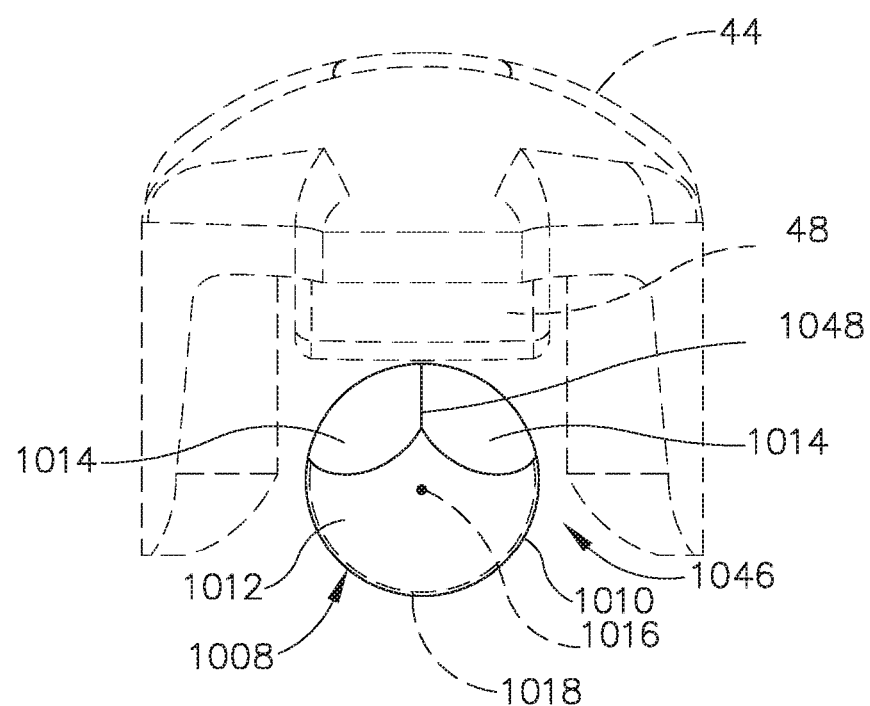
FIG. 37 depicts a distal end view of the ultrasonic blade of FIG. 36.

FIGS. 36-37 show a first example of a circumferential blade profile of (1008) of an ultrasonic blade (1046) with a first backcutting edge (1048) configured to backcut tissue about a minority of circumferential blade profile (1008) and further configured to seal tissue about a majority of circumferential blade profile (1008). Blade (1046) of the present example more particularly includes a blade body (1010) distally extending to a partially hemispherical distal end tip (1012). A pair of laterally, longitudinally, and transversely swept grooves (1014) extend through partially hemispherical distal end tip (1012) as well as a portion of blade body (1010) to define backcutting edge (1048) along blade (1046). As shown in the present example, a majority of a longitudinal length of backcutting edge (1048) is positioned on partially hemispherical distal end tip (1012) rather than blade body (1010). More particularly, all of the longitudinal length of backcutting edge (1048) is positioned on partially hemispherical distal end tip (1012) in the present example such that no portion of backcutting edge (1048) is positioned on blade body (1010) despite some proximal portion of swept grooves (1014) being on blade body (1010).

As more particularly shown in FIG. 37, backcutting edge (1048) longitudinally extends through a transversely extending plane also in alignment with a central blade axis (1016). Swept grooves (1014) are thus laterally symmetric about this transversely extending plane. Circumferential blade profile (1008) of the present example is circular about an entirety of central blade axis (1016) such that clamp pad (48) extends as a tangent about blade (1046) in any angular position about blade (1046) but for portions of clamp pad (48) adjacent to swept grooves (1014), thereby defining a circumferential sealing profile (1018). Circumferential sealing profile (1018) is thus arcuate and angularly surrounds a majority of central blade axis (1016), such as greater than 180 degrees, without surrounding portions that include swept grooves (1014) and backcutting edge (1048). Circumferential sealing profile (1018) thereby represents the rounded surfaces along partially hemispherical distal end tip (1012) configured for sealing tissue against clamp pad (48). It will be appreciated that backcutting edge (1048) and swept grooves (1014) may vary while still providing circumferential sealing profile (1018) about the majority of central blade axis (1016). The invention is thus not intended to be limited to the particular backcutting edge (1048) and swept grooves (1014) shown in the present example.

In use for sealing tissue, the operator selectively rotates clamp arm (44) relative to blade (1046) to position clamp pad (48) in any desirable angular position radially inline with circumferential sealing profile (1018). In turn, tissue is received between clamp pad (48) and blade (1046) against circumferential sealing profile (1018), and clamp arm (44) pivots from the open position to the closed position for clamping tissue against blade (1046). The operator selectively actives blade (1046) with ultrasonic vibrations in order to seal tissue clamped between clamp pad (48) and clamp arm (44). In the event that the operator desires to selectively backcut tissue, clamp arm (44) is positioned away from backcutting edge (1048) such that backcutting edge (1048) is relatively exposed. The operator then directly engages tissue with backcutting edge (1048) for backcutting the tissue as desired.

In one example, clamp arm (44) is further configured to only radially align with the circumferential sealing profile (1018) in order to inhibit the operator from inadvertently moving clamp pad (48) toward direct engagement with backcutting edge (1048). Clamp arm (44) may have mechanical stops (not shown) and/or associated software configured to inhibit such rotation. Of course, the invention is not intended to be unnecessarily limited to include such alignment constraints and, in some examples, clamp arm (44) is free to move to any angular position about blade (1046).

B. Second Exemplary Backcutting Edge

Figure 38:
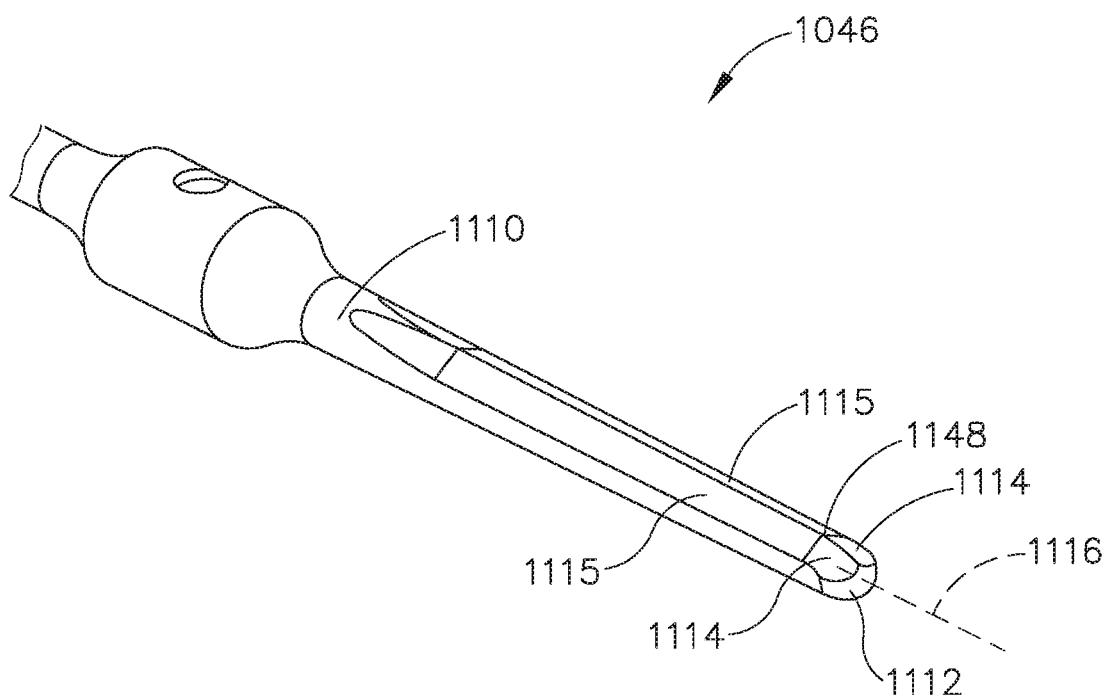
FIG. 38 depicts a perspective view of another ultrasonic blade with a second example of a circumferential blade profile having a second backcutting edge.
Figure 39:
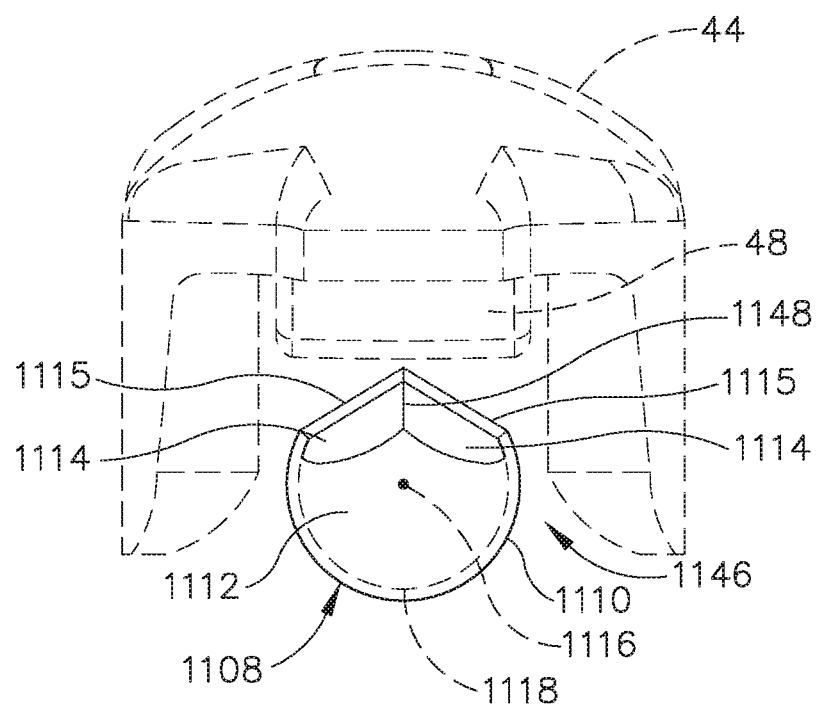
FIG. 39 depicts a distal end view of the ultrasonic blade of FIG. 38.

FIGS. 38-39 show a third example of a circumferential blade profile of (1108) of an ultrasonic blade (1146) with a second backcutting edge (1148) configured to backcut tissue about a minority of circumferential blade profile (1108) and further configured to seal tissue about a majority of circumferential blade profile (1108). Blade (1146) of the present example more particularly includes a blade body (1110) distally extending to partially hemispherical distal end tip (1112). A pair of laterally, longitudinally, and transversely swept grooves (1114) extend through partially hemispherical distal end tip (1012). In addition, a pair of laterally, longitudinally, and transversely swept grooves (1115) extend along blade body (1010). Swept grooves (1114) and grooves (1115) collectively define backcutting edge (1148) along blade (1146). As shown in the present example, a majority of a longitudinal length of backcutting edge (1148) is positioned on blade body (1110) such that backcutting edge (1148) extends along majority of a length of blade (1146).

As more particularly shown in FIG. 39, backcutting edge (1148) longitudinally extends through a transversely extending plane also in alignment with a central blade axis (1116). Swept grooves (1114, 1115) are thus laterally symmetric about this transversely extending plane. Circumferential blade profile (1108) of the present example is circular about an angular majority of central blade axis (1016) such that clamp pad (48) extends as a tangent about blade (1046) in this angular majority about blade (1046) but for portions of clamp pad (48) adjacent to swept grooves (1114, 1115), thereby defining a circumferential sealing profile (1118). Circumferential sealing profile (1118) is thus arcuate and angularly surrounds a majority of central blade axis (1116), such as greater than 180 degrees, without surrounding portions that include swept grooves (1114, 1115) and backcutting edge (1148). Circumferential sealing profile (1118) thereby represents the rounded surfaces along partially hemispherical distal end tip (1112) configured for sealing tissue against clamp pad (48). It will be appreciated that backcutting edge (1148) and swept grooves (1114, 1115) may vary while still providing circumferential sealing profile (1118) about the majority of central blade axis (1116). The invention is thus not intended to be limited to the particular backcutting edge (1148) and swept grooves (1114, 1115) shown in the present example.

In use for sealing tissue, the operator selectively rotates clamp arm (44) relative to blade (1146) to position clamp pad (48) in any desirable angular position radially inline with circumferential sealing profile (1118). In turn, tissue is received between clamp pad (48) and blade (1146) against circumferential sealing profile (1118), and clamp arm (44) pivots from the open position to the closed position for clamping tissue against blade (1146). The operator selectively actives blade (1146) with ultrasonic vibrations in order to seal tissue clamped between clamp pad (48) and clamp arm (44). In the event that the operator desires to selectively backcut tissue, clamp arm (44) is positioned away from backcutting edge (1148) such that backcutting edge (1148) is relatively exposed. The operator then directly engages tissue with backcutting edge (1148) for backcutting the tissue as desired.

In one example, clamp arm (44) is further configured to only radially align with the circumferential sealing profile (1118) in order to inhibit the operator from inadvertently moving clamp pad (48) toward direct engagement with backcutting edge (1148). Clamp arm (44) may have mechanical stops (not shown) and/or associated software configured to inhibit such rotation. Of course, the invention is not intended to be unnecessarily limited to include such alignment constraints and, in some examples, clamp arm (44) is free to move to any angular position about blade (1146).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An acoustic waveguide for an ultrasonic surgical instrument, comprising: (a) a proximal waveguide body portion defining a longitudinal axis; (b) a distal waveguide body portion having an ultrasonic blade distally projecting therefrom; and (c) an articulation body portion extending between the proximal and distal waveguide body portions, wherein the articulation body portion is configured to flex a first direction to thereby deflect the ultrasonic blade relative to the longitudinal axis and through a first plane, wherein the articulation body portion is further configured to flex a second direction to thereby deflect the ultrasonic blade relative to the longitudinal axis and through a second plane, and wherein the second direction is different than the first direction such that the second plane is different than the first plane for multiplanar deflection of the ultrasonic blade relative to the longitudinal axis.

Example 2

The acoustic waveguide of Example 1, wherein the second plane is perpendicular to the first plane.

Example 3

The acoustic waveguide of any one or more of Examples 1 through 2, wherein the articulation body portion includes a first flexible member.

Example 4

The acoustic waveguide of Example 3, wherein the first flexible member is a flexible member configured to receive an acoustic vibration from the proximal waveguide body portion, and communicate the acoustic vibration from the proximal waveguide body portion to the distal waveguide body portion for driving the ultrasonic blade with the acoustic vibration.

Example 5

The acoustic waveguide of any one or more of Examples 3 through 4, wherein the first flexible member has a set of predetermined properties and the acoustic vibration has a longitudinal vibrational component and a transverse vibrational component, and wherein the set of predetermined properties of the first flexible member are configured to uncouple the longitudinal vibrational component from the transverse vibrational component thereby communicating the acoustic vibration from the proximal waveguide body portion to the distal waveguide bod portion for driving the ultrasonic blade with the acoustic vibration.

Example 6

The acoustic waveguide of any one or more of Examples 3 through 5, wherein the first flexible member is a flexible wire.

Example 7

The acoustic waveguide of Example 6, wherein the flexible wire has a wire cross-sectional radius, the proximal waveguide body portion has a proximal waveguide radius, and the distal waveguide body portion has a distal waveguide radius, and wherein the wire cross-sectional radius is smaller than the proximal and distal waveguide radii.

Example 8

The acoustic waveguide of any one or more of Examples 6 through 7, wherein the flexible wire is positioned on a node.

Example 9

The acoustic waveguide of any one or more of Examples 6 through 8, wherein the flexible wire is centered on the node.

Example 10

The acoustic waveguide of any one or more of Examples 3 through 10, wherein the first flexible member is formed as a single, unitary structure with the proximal and distal waveguide body portions.

Example 11

The acoustic waveguide of any one or more of Examples 3 through 10, wherein the first flexible member is affixed to the proximal waveguide body portion at a proximal component joint, and wherein the first flexible member is affixed to the distal waveguide body portion at a distal component joint.

Example 12

The acoustic waveguide of any one or more of Examples 3 through 11, wherein the articulation body portion includes a second flexible member

Example 13

The acoustic waveguide of Example 12, wherein the first flexible member is a first flexible ribbon, and wherein the second flexible member is a second ribbon.

Example 14

The acoustic waveguide of any one or more of Examples 1 through 13, wherein the ultrasonic blade extends along a blade axis and has a blade body defining a circumferential blade profile about the blade axis, and wherein the ultrasonic blade includes a backcutting edge longitudinally extending along the blade body such that the circumferential blade profile is circular about a majority of the circumferential blade profile and configured to seal against a clamp pad.

Example 15

The acoustic waveguide of Example 14, wherein the blade body has a distal blade portion that tapers to a distal blade tip, and wherein at least a majority of the backcutting edge longitudinally extends along the distal blade portion that tapers to the distal blade tip.

Example 16

An ultrasonic surgical instrument, comprising: (a) an end effector including an ultrasonic blade; (b) a body assembly; and (c) a shaft assembly having a first articulation section and longitudinally extending from the body assembly to the end effector, including: (i) a proximal waveguide body portion positioned proximally from the first articulation section and defining a longitudinal axis, (ii) a distal waveguide body portion positioned distally from the first articulation section and in acoustic communication with the ultrasonic blade distally projecting therefrom, and (iii) an articulation body portion extending through the first articulation section between the proximal and distal waveguide body portions, wherein the articulation body portion is configured to flex a first direction to thereby deflect the ultrasonic blade relative to the longitudinal axis and through a first plane, and wherein the articulation body portion is further configured to flex a second direction to thereby deflect the ultrasonic blade relative to the longitudinal axis and through a second plane, wherein the second direction is different than the first direction such that the second plane is different than the first plane for multiplanar deflection of the ultrasonic blade relative to the longitudinal axis.

Example 17

The ultrasonic surgical instrument of Example 16, wherein the articulation body portion includes a first flexible member, and wherein the first articulation section of the shaft assembly is configured to limit the first flexible member to a predetermined maximum bend radius.

Example 18

The ultrasonic surgical instrument of Example 16, wherein the articulation body portion includes a first flexible member and a second flexible member, wherein the shaft assembly further includes a second articulation section, and wherein the first and second flexible members are positioned in the first and second articulation sections.

Example 19

The ultrasonic surgical instrument of any one or more of Examples 16 through 18, wherein the body assembly further includes a robotic driven interface operatively connected to the articulation body portion and configured to connect to a robotic drive for selectively directing flexing of the articulation body portion in the first or second directions.

Example 20

A method of deflecting an end effector of an ultrasonic surgical instrument, wherein the ultrasonic surgical instrument has an acoustic waveguide including (a) a proximal waveguide body portion defining a longitudinal axis; (b) a distal waveguide body portion having an ultrasonic blade distally projecting therefrom; and (c) an articulation body portion extending between the proximal and distal waveguide body portions, the method comprising: (a) flexing the articulation body portion in a first direction to thereby deflect the ultrasonic blade relative to the longitudinal axis and through a first plane; and (b) flexing the articulation body portion in a second direction different than the first direction to thereby deflect the ultrasonic blade relative to the longitudinal axis and through a second plane different than the first plane.

Example 21

An ultrasonic surgical instrument, comprising: (a) an end effector including an ultrasonic blade; (b) a body assembly; and (c) a shaft assembly, including (i) a proximal shaft portion defining a longitudinal axis, (ii) a distal shaft portion, and (iii) an articulation section extending between the proximal and distal shaft portion, wherein the articulation section is configured to articulate a first direction to thereby deflect the ultrasonic blade relative to the longitudinal axis and through a first plane, and wherein the articulation section is further configured to articulate a second direction to thereby deflect the ultrasonic blade relative to the longitudinal axis and through a second plane, wherein the second direction is different than the first direction such that the second plane is different than the first plane for multiplanar deflection of the ultrasonic blade relative to the longitudinal axis.

Example 22

The ultrasonic surgical instrument of Example 21, wherein the articulation section includes a plurality of links configured to pivot relative to each other to thereby articulate in the first direction or the second direction.

Example 23

An end effector of an ultrasonic surgical instrument, comprising: (a) an ultrasonic blade, wherein the ultrasonic blade extends along a blade axis and has a blade body defining a circumferential blade profile about the blade axis, and wherein the ultrasonic blade includes a backcutting edge longitudinally extending along the blade body such that the circumferential blade profile is circular about a majority of the circumferential blade profile and configured engage a clamp pad.

Example 24

The end effector of Example 23, wherein the blade body has a distal blade portion that tapers to a distal blade tip, and wherein at least a majority of the backcutting edge longitudinally extends along the distal blade portion that tapers to the distal blade tip.

V. Miscellaneous

Any one or more of the teaching, expressions, embodiments, examples, etc. described herein may be combined with any one or more of the teachings, expressions, embodiments, examples, etc. described in U.S. patent application Ser. No. 16/556,667, entitled "Ultrasonic Transducer Alignment of an Articulating Ultrasonic Surgical Instrument," filed on Aug. 30, 2019, published as U.S. Pub. No. 2021/0059710 on Mar. 4, 2021; U.S. patent application Ser. No. 16/556,625, entitled "Ultrasonic Surgical Instrument with Axisymmetric Clamping," filed on Aug. 30, 2019, issues as U.S. Pat. No. 11,471,181 on Oct. 18, 2022; U.S. patent application Ser. No. 16/556 635, entitled "Ultrasonic Blade and Clamp Arm Alignment Features," filed Aug. 30, 2019, issued as U.S. Pat. No. 11,457,945 on Oct. 4, 2022; and/or U.S. patent application Ser. No. 16/556 727, entitled "Rotatable Linear Actuation Mechanism," filed Aug. 30, 2019, published as U S. Pub. No. 2021/0059711 on Mar. 4, 2021. The disclosure of each of these applications is incorporated by reference herein.

It should be understood that any of the versions of instruments described herein may include various other features in addition to or in lieu of those described above. By way of example only, in addition to the teachings above, it should be understood that the instruments described herein may be constructed and operable in accordance with at least some of the teachings of U.S. Pat. Nos. 5,322,055; 5,873,873; 5,980,510; 6,325,811; 6,773,444; 6,783,524; 9,095,367; U.S. Pub. No. 2006/0079874; U.S. Pub. No. 2007/0191713; U.S. Pub. No. 2007/0282333; U.S. Pub. No. 2008/0200940; U.S. Pat. No. 8,623,027, issued Jan. 7, 2014; U.S. Pat. No. 9,023,071, issued May 5, 2015; U.S. Pat. No. 8,461,744, issued Jun. 11, 2013; U.S. Pat. No. 9,381,058, issued Jul. 5, 2016; U.S. Pub. No. 2012/0116265; U.S. Pat. No. 9,393,037, issued Jul. 19, 2016; U.S. Pat. No. 10,172,636, issued Jan. 8, 2019; and/or U.S. Pat. App. No. 61/410,603. The disclosures of each of the foregoing patents, publications, and applications are incorporated by reference herein. It should also be understood that the instruments described herein may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, the instruments described herein may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS®

Ultrasonic Shears, and/or the HARMONIC SYNERGY® Ultrasonic Blades, and the teachings herein relating to the instruments described herein, there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into another example of a robotic surgical system, and those of ordinary skill in the art will recognize that various teachings herein may be readily combined with various teachings of any of the following: U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An acoustic waveguide for an ultrasonic surgical instrument, comprising:
   (a) a proximal waveguide body portion defining a longitudinal axis;
   (b) a distal waveguide body portion having an ultrasonic blade distally projecting therefrom; and
   (c) an articulation body portion extending along a centerline between the proximal and distal waveguide body portions, the articulation body portion comprising:
      (i) a first flexible member having a first outer surface, wherein the first flexible member defines a first radial dimension about the centerline extending from the centerline to the first outer surface,
      (ii) a second flexible member having a second outer surface, wherein the first flexible member defines a second radial dimension about the centerline extending from the centerline to the second outer surface, and
      (iii) a central portion positioned between the first flexible member and the second flexible member and having a central outer surface, wherein the central portion defines a central radial dimension about the centerline extending from the centerline to the central outer surface, wherein the central radial dimension is larger than each of the first and second radial dimensions, wherein the articulation body portion is configured to flex at the first flexible member a first direction to thereby deflect the ultrasonic blade relative to the longitudinal axis and through a first plane, wherein the articulation body portion is further configured to flex at the second flexible member a second direction to thereby deflect the ultrasonic blade relative to the longitudinal axis and through a second plane, wherein the second direction is different than the first direction such that the second plane is different than the first plane for multiplanar deflection of the ultrasonic blade relative to the longitudinal axis, wherein the articulation body portion is removably coupled to either the proximal waveguide body portion or the distal waveguide body portion.

2. The acoustic waveguide of claim 1, wherein the second plane is perpendicular to the first plane.

3. The acoustic waveguide of claim 1, wherein the first flexible member is a flexible member configured to receive an acoustic vibration from the proximal waveguide body portion and communicate the acoustic vibration from the proximal waveguide body portion to the distal waveguide body portion for driving the ultrasonic blade with the acoustic vibration.

4. The acoustic waveguide of claim 3, wherein the first flexible member has a set of predetermined properties and the acoustic vibration has a longitudinal vibrational component and a transverse vibrational component, and wherein the set of predetermined properties of the flexible member are configured to uncouple the longitudinal vibrational component from the transverse vibrational component thereby communicating the acoustic vibration from the proximal waveguide body portion to the distal waveguide body portion for driving the ultrasonic blade with the acoustic vibration.

5. The acoustic waveguide of claim 4, wherein the first flexible member is a flexible wire.

6. The acoustic waveguide of claim 5, wherein the flexible wire has a wire cross-sectional radius, the proximal waveguide body portion has a proximal waveguide radius, and the distal waveguide body portion has a distal waveguide radius, and wherein the wire cross-sectional radius is smaller than the proximal and distal waveguide radii.

7. The acoustic waveguide of claim 5, wherein the flexible wire is positioned on a node.

8. The acoustic waveguide of claim 7, wherein the flexible wire is centered on the node.

9. The acoustic waveguide of claim 1, wherein the first flexible member is formed as a single, unitary structure with the proximal and distal waveguide body portions.

10. The acoustic waveguide of claim 1, wherein the first flexible member is affixed to the proximal waveguide body portion at a proximal component joint, and wherein the first flexible member is affixed to the distal waveguide body portion at a distal component joint.

11. The acoustic waveguide of claim 1, wherein the first flexible member is a first flexible ribbon, and wherein the second flexible member is a second flexible ribbon.

12. The acoustic waveguide of claim 1, wherein the ultrasonic blade extends along a blade axis and has a blade body defining a circumferential blade profile about the blade axis, and wherein the ultrasonic blade includes a backcutting edge longitudinally extending along the blade body such that the circumferential blade profile is circular about a majority of the circumferential blade profile and configured to engage a clamp pad.

13. The acoustic waveguide of claim 12, wherein the blade body has a distal blade portion that tapers to a distal blade tip, and wherein at least a majority of the backcutting edge longitudinally extends along the distal blade portion that tapers to the distal blade tip.

14. The acoustic waveguide of claim 1, wherein the first flexible member includes a first circular cross-section, and wherein the second flexible member includes a second circular cross-section.

15. An ultrasonic surgical instrument, comprising:
(a) an end effector including an ultrasonic blade;
(b) a body assembly; and
(c) a shaft assembly having a first articulation section and longitudinally extending from the body assembly to the end effector, including:
   (i) a proximal waveguide body portion positioned proximally from the first articulation section and defining a longitudinal axis,
   (ii) a distal waveguide body portion positioned distally from the first articulation section and in acoustic communication with the ultrasonic blade distally projecting therefrom,
   (iii) an articulation body portion extending through the first articulation section between the proximal and distal waveguide body portions,
   wherein the articulation body portion is configured to flex a first direction to thereby deflect the ultrasonic blade relative to the longitudinal axis and through a first plane,
   wherein the articulation body portion is further configured to flex a second direction to thereby deflect the ultrasonic blade relative to the longitudinal axis and through a second plane,
   wherein the second direction is different than the first direction such that the second plane is different than the first plane for multiplanar deflection of the ultrasonic blade relative to the longitudinal axis,
   wherein the articulation body portion includes a first flexible member defining a cross-sectional radius, and
   wherein the first articulation section of the shaft assembly is configured to limit the first flexible member to a predetermined maximum bend radius, wherein the predetermined maximum bend radius relates to the cross-sectional radius according to a first condition for uncoupling a longitudinal vibrational component from a transverse vibrational component to communicate an acoustic vibration from the proximal waveguide body portion to the distal waveguide body portion and driving the ultrasonic blade with the acoustic vibration,
   wherein the first condition is the cross-sectional radius divided by the predetermined maximum bend radius is less than 0.1.

16. The ultrasonic surgical instrument of claim 15, wherein the body assembly further includes a robotic driven interface operatively connected to the articulation body portion and configured to connect to a robotic drive for selectively directing flexing of the articulation body portion in the first or second directions.

17. The ultrasonic surgical instrument of claim 15, wherein the predetermined maximum bend radius relates to the cross-sectional radius according to a second condition for uncoupling the longitudinal vibrational component from the transverse vibrational component to communicate the acoustic vibration from the proximal waveguide body portion to the distal waveguide body portion and driving the ultrasonic blade with the acoustic vibration, wherein the second condition is $$R > c/(2*\pi*f)$$

where:
R is the predetermined maximum bend radius;
c is the speed of sound;
π is pi; and
f is a natural frequency of the first flexible member.

18. The ultrasonic surgical instrument of claim 17, wherein the predetermined maximum bend radius relates to the cross-sectional radius according to a third condition for uncoupling the longitudinal vibrational component from the transverse vibrational component to communicate the acoustic vibration from the proximal waveguide body portion to the distal waveguide body portion and driving the ultrasonic blade with the acoustic vibration, wherein the third condition is $$(8*E*r)/(\pi^{2}*R) < \sigma_y$$

where:
E is an elastic module of the first flexible member;
r is the cross-sectional radius of the first flexible member;
πC is pi;
R is the predetermined maximum bend radius; and
$\sigma_y$ is a yield strength of the first flexible member.

19. A method of deflecting an end effector of an ultrasonic surgical instrument, wherein the ultrasonic surgical instrument has an acoustic waveguide including (a) a proximal waveguide body portion defining a longitudinal axis; (b) a distal waveguide body portion having an ultrasonic blade distally projecting therefrom; and (c) an articulation body portion with a cross-sectional radius and extending between the proximal and distal waveguide body portions, the method comprising:
 (a) flexing the articulation body portion in a first direction to form a bend radius to thereby deflect the ultrasonic blade relative to the longitudinal axis and through a first plane;
 (b) limiting the bend radius to a predetermined maximum bend radius according to a first condition, wherein the first condition is the cross-sectional radius divided by the predetermined maximum bend radius is less than 0.1; and
 (c) uncoupling a longitudinal vibrational component from a transverse vibrational component to communicate an acoustic vibration from the proximal waveguide body portion to the distal waveguide body portion thereby driving the ultrasonic blade with the acoustic vibration.

* * * * *